USOO8222026B2

(12) United States Patent
Tsai et al.

(10) Patent No.: US 8,222,026 B2
(45) Date of Patent: Jul. 17, 2012

(54) STACKED ARRAY BIOREACTOR FOR CONVERSION OF SYNGAS COMPONENTS TO LIQUID PRODUCTS

(75) Inventors: Shih-Perng Tsai, Naperville, IL (US); Rathin Datta, Chicago, IL (US); Rahul Basu, Naperville, IL (US); Seong-Hoon Yoon, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 253 days.

(21) Appl. No.: 12/258,180

(22) Filed: Oct. 24, 2008

(65) Prior Publication Data
US 2009/0215153 A1 Aug. 27, 2009

Related U.S. Application Data

(63) Continuation-in-part of application No. 12/036,007, filed on Feb. 22, 2008.

(51) Int. Cl.
*C12M 1/12* (2006.01)
*C12M 1/00* (2006.01)
*C12M 3/00* (2006.01)
(52) U.S. Cl. ........ 435/297.2; 435/284.1; 435/287.8; 435/293.1; 435/297.1; 435/299.1; 435/304.1; 435/305.1
(58) Field of Classification Search ........ 435/297.2, 435/284.1, 287.8, 293.1, 297.1, 299.1, 304.1, 435/305.1
See application file for complete search history.

(56) References Cited

U.S. PATENT DOCUMENTS

| 4,181,604 | A | 1/1980 | Onishi et al. |
| 4,442,206 | A | 4/1984 | Michaels et al. |
| 4,746,435 | A | 5/1988 | Onishi et al. |
| 5,106,506 | A | 4/1992 | Schmidt et al. |
| 5,173,429 | A | 12/1992 | Gaddy et al. |
| 5,753,474 | A | 5/1998 | Ramey |
| 5,938,922 | A * | 8/1999 | Fulk et al. ........ 210/321.81 |
| 6,043,392 | A | 3/2000 | Holtzapple et al. |
| 6,136,577 | A | 10/2000 | Gaddy |
| 6,340,581 | B1 | 1/2002 | Gaddy |
| 6,387,262 | B1 | 5/2002 | Rittmann et al. |

(Continued)

FOREIGN PATENT DOCUMENTS
WO WO0208438 A2 1/2002
(Continued)

OTHER PUBLICATIONS

Clausen, E.C., et al., "Ethanol From Biomass by Gasification/Fermentation", Presented at Plastics, Tires, Auto Wastes/Biomass MSW Symposium, Fall 1993, Chicago, 38 (3).

(Continued)

*Primary Examiner* — Nathan Bowers

(57) ABSTRACT

A membrane supported bioreactor arrangement and method for anaerobic conversion of gas into liquid products including membrane modules having hollow fibers packed across a cross sectional area of the membrane module, each of the hollow fibers formed from an asymmetric membrane wall having a porous outer layer defining biopores for retaining a porous biolayer about the outer surface of the membrane wall and a less permeable hydration layer around the hollow fiber lumen; a membrane vessel for surrounding the outside of the hollow fibers with a process gas from a gas supply conduit; and a liquid supply conduit operably connected to the hollow fibers for supplying a process liquid to the hollow fiber lumens. The gas supply conduit enables the formation of a biolayer on the outer surface of the hollow fiber wall by interaction of microorganisms with the process gas and the production of a liquid product.

14 Claims, 11 Drawing Sheets

U.S. PATENT DOCUMENTS

| | | |
|---|---|---|
| 6,558,549 B2 | 5/2003 | Cote et al. |
| 6,844,187 B1* | 1/2005 | Wechsler et al. ......... 435/297.2 |
| 6,908,547 B2 | 6/2005 | Cote et al. |
| 6,919,488 B2 | 7/2005 | Melnichuk et al. |
| 7,118,672 B2 | 10/2006 | Husain et al. |
| 7,169,295 B2 | 1/2007 | Husain et al. |
| 7,189,323 B2 | 3/2007 | Lofqvist et al. |
| 7,285,402 B2 | 10/2007 | Gaddy et al. |
| 7,704,723 B2 | 4/2010 | Huhnke et al. |
| 2003/0211585 A1* | 11/2003 | Gaddy et al. ............... 435/161 |
| 2004/0045890 A1* | 3/2004 | Herczeg ..................... 210/321.8 |
| 2004/0065607 A1* | 4/2004 | Wang et al. ............... 210/500.41 |
| 2005/0054087 A1 | 3/2005 | Cote et al. |
| 2005/0082227 A1* | 4/2005 | Cote et al. ..................... 210/650 |
| 2005/0260739 A1* | 11/2005 | Rosen et al. ............. 435/254.21 |
| 2006/0014274 A1* | 1/2006 | Klaus ......................... 435/297.4 |
| 2006/0021936 A1 | 2/2006 | Husain et al. |
| 2006/0037896 A1 | 2/2006 | Cote et al. |
| 2006/0163157 A1 | 7/2006 | Cote et al. |
| 2007/0275447 A1 | 11/2007 | Lewis et al. |
| 2008/0305539 A1 | 12/2008 | Hickey et al. |
| 2008/0305540 A1 | 12/2008 | Hickey et al. |
| 2009/0029434 A1 | 1/2009 | Tsai et al. |
| 2009/0035848 A1 | 2/2009 | Hickey et al. |
| 2009/0104676 A1 | 4/2009 | Tsai et al. |
| 2009/0215139 A1 | 8/2009 | Datta et al. |
| 2009/0215142 A1 | 8/2009 | Tsai et al. |
| 2009/0215153 A1 | 8/2009 | Tsai et al. |
| 2009/0215163 A1 | 8/2009 | Tsai et al. |
| 2009/0286296 A1 | 11/2009 | Hickey et al. |
| 2010/0105116 A1 | 4/2010 | Datta et al. |

FOREIGN PATENT DOCUMENTS

| | | |
|---|---|---|
| WO | WO2008154301 | 12/2008 |

OTHER PUBLICATIONS

Klasson, K.T., et al., "Biological Production of Liquid and Gaseous Fuels from Synthesis Gas," Appl. Biochem. Biotechnol., vol. 24-25, No. 1, Mar. 1990, 857-873.

Vega, J. L., et al., "The Biological Production of Ethanol from Synthesis Gas," Appl. Biochem. Biotechnol. vol. 20-21, No. 1, Jan. 1989, 781-797.

Phillips, John R., et al., "Synthesis Gas as Substrate for the Biological Production of Fuels and Chemicals," Appl. Biochem. Biotechnol. vol. 45-46, No. 1, Mar. 1994, 145-157.

Barik, S., et al., "Biological Production of Alcohols from Coal Through Indirect Liquefaction," Appl. Biochem. Biotechnol. vol. 18, No. 1, Aug. 1988, 363-387.

Popular Mechanics, Coskata Ethanol Technology—How it Works—Illustration and Analysis, http://www.popularmechanics.com/science/research/4248759.html?series=19, Feb. 22, 2008, pp. 1-3.

Ethanol Production by *Saccharomyces cerevisiae* Immobilized in Hollow-Fiber Membrane Bioreactors, Douglas S. Inloes, et al., Applied and Environmental Microbiology, Jul. 1983, pp. 264-278, vol. 46. No. 1.

"Evidence for Production of n-Butanol from Carbon Monoxide by *Butyribacterium methylotrophicum*," Journal of Fermentation and Bioengineering, vol. 72, 1991, p. 58-60.

"Production of butanol and ethanol from synthesis gas via fermentation," Fuel, vol. 70, May 1991, p. 615-619.

Das, A. and L.G. Ljungdahl, Electron Transport Systems in Acetogens, Chapter 14, in Biochemistry and Physiology of Anaerobic Bacteria, L.G. Ljungdahl et al eds., Springer (2003).

Drake, H.L. and K. Kusel, Diverse Physiologic Potential of Acetogens, Chapter 13, in Biochemistry and Physiology of Anaerobic Bacteria, L.G. Ljungdahl et al eds., Springer (2003).

Muller, V., Minireview: Energy Conservation in Acetogenic Bacteria, Applied and Environmental Microbiology, vol. 69, 11, 6345-53, Nov. 2003.

Innovations in Wastewater Treatment: The moving bed biofilm process. Water Science and Technology vol. 53 No. 9 pp. 17-33.

Rahtin Datta and J.G. Zeikus, Anaerobic Conversion of One-Carbon Compounds. vol. 24 of Developments in Industrial Microbiology, 1983.

Datta et al, Reprinted from vol. 24 of Developments in Industrial Microbilogy, a Publication of the Society for Industrial Microbiology—1985, Chapter 10, Anaerobic Bioconversion of One-Carbon Compounds, pp. 1-6.

Kim et al, Plant Cell Immobilization in a Dual Hollow Fiber Bioreactor, Biotechnology Techniques vol. 3 No. 2, 1989, pp. 139-144.

Inloes, D. S, et al, Hollow-Fiber Membrane Bioreactors Using Immobilized *E. coli* for Protein Synthesis, pp. 2653-2681.

Nloes, D. S. et al, Ethanol Production by *Saccharomyces cerevisiae* Immobilized in Hollow-Fiber Membrane Bioreactors, Accepted Apr. 25, 1983, Applied and Environmental Microbiology, Jul. 1983, vol. 46. No. 1, pp. 264-278.

Henstra, A. M. et al, Microbiology of Synthesis Gas Fermentation for Biofuel Production, ScienceDirect, Current Opinion in Biotechnology 2007, 18:200-206.

* cited by examiner

STACKED ARRAY BIOREACTOR FOR CONVERSION OF SYNGAS COMPONENTS TO LIQUID PRODUCTS

CROSS REFERENCE TO RELATED APPLICATION(S)

This application is a continuation-in-part of U.S. patent application Ser. No. 12/036,007, filed on Feb. 22, 2008, entitled SYNGAS CONVERSION SYSTEM USING ASYMMETRIC MEMBRANE AND ANAEROBIC MICROORGANISM, and claims priority therefrom, and incorporates herein the teachings thereof by reference.

FIELD OF THE INVENTION

This invention relates to the conversion of gas streams into liquid products using conversion modules that define separate gas and liquid contacting surfaces.

DETAILED DESCRIPTION

Background

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$, and $CO_2$ with other components such as $CH_4$, $N_2$, $NH_3$, $H_2S$, and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste, and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

$$6CO + 3H_2O \rightarrow C_2H_5OH + 4CO_2$$

$$6H_2 + 2CO_2 \rightarrow C_2H_5OH + 3H_2O$$

Thus 6 moles of relatively insoluble gases such as CO or $H_2$ have to transfer to an aqueous medium for each mole of ethanol. Other products such as acetic acid and n-butanol have similar large stoichiometric requirements for the gases.

Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance. To get high yields and production rates the cell concentrations in the bioreactor need to be high and this requires some form of cell recycle or retention.

Many devices and equipment are used for gas transfer to microorganisms in fermentation and waste treatment applications. These numerous bioreactors all suffer from various drawbacks. In most of these conventional bioreactors and systems, agitators with specialized blades or configurations are used. In some others such as gas lift or fluidized beds, liquids or gases are circulated via contacting devices. The agitated vessels require a lot of mechanical power often in the range of 4 to 10 KW per 1000 gallons—uneconomical and unwieldy for large scale fermentations that will be required for such syngas bioconversions. The fluidized or fluid circulating systems cannot provide the required gas dissolution rates. Furthermore, most of these reactors or systems are configured for use with microorganisms in planktonic form, i.e., they exist as individual cells in liquid medium.

Existing bioreactors are either small scale, unsuitable for large scale manufacturing processes, or custom designed, increasing manufacturing and installation costs. Submerged membrane modules for wastewater treatment, such as the Puron MBR Module Model PSH-1500 from Koch Membrane Systems (Wilmington, Mass.), have been used in water and wastewater treatment for filtration and biological wastewater treatment. Wastewater and sludge is maintained outside a fiber of microporous hydrophilic membrane, and water is drawn into the center of the fiber through the microporous hydrophilic membrane to become treated water. Water fills both the shell side and center of the hollow fibers.

To get high yields and production rates the cell concentrations in the bioreactor need to be high and this requires some form of cell recycle or retention. Conventionally, this is achieved by filtration of the fermentation broth through microporous or nonporous membranes, returning the cells and purging the excess. These systems are expensive and require extensive maintenance and cleaning of the membranes to maintain the fluxes and other performance parameters.

Cell retention by formation of biofilms is a very good and often inexpensive way to increase the density of microorganisms in bioreactors. This requires a solid matrix with large surface area for the microorganisms to colonize and form a biofilm that contains the metabolizing microorganisms in a matrix of biopolymers that the microorganisms generate. Trickle bed and some fluidized bed bioreactors make use of biofilms to retain microorganisms on solid surfaces while providing dissolved gases in the liquid by flow past the solid matrix. They suffer from either being very large or unable to provide sufficient gas dissolution rates. Particular forms of membranes have found use in supporting specific types of microorganisms for waste water treatment processes. U.S. Pat. No. 4,181,604 discloses the use of hollow fiber membranes for waste treatment where the outer surface of the fibers supports a layer of microorganisms for aerobic digestion of sludge.

U.S. patent application Ser. No. 11/781,717, filed Jul. 23, 2007; U.S. patent application Ser. No. 11/833,864, filed Aug. 3, 2007; and U.S. patent application Ser. No. 11/972,454, filed Jan. 10, 2008, disclose a membrane based bioreactor wherein anaerobic bacteria that have the ability to convert syngas to ethanol or other liquids have formed biofilms on the outer surface of hydrophobic membranes with the syngas fed to the bacterial biofilm through the inner surface of the membrane. Such a bioreactor system has been able to directly convert the primary components of synthesis gas, CO, and $H_2/CO_2$ to ethanol and other liquid products such as n-butanol, acetic acid, and butyric acid. In these systems the gas flows through a porous region of a hydrophobic membrane and then reaches a biofilm which is hydrophilic. One drawback of this arrangement is that if water reaches and deposits/condenses on the hydrophobic porous region it will severely decrease the gas transfer rate. When the biofilm grows on the outside of a hollow fiber membrane, this type of membrane system also lacks a direct means to promote the formation of a biofilm with an adequate thickness and control its performance.

Asymmetric membranes are known for use in a variety of membrane separations processes such as ultra and nano filtration. Asymmetric membranes are typically hydrophilic and have a relatively tight semi permeable "skin" layer on one side supported on a porous polymer layer. U.S. Pat. Nos. 4,442,206 and 4,440,853 show the use of the polymer layer in an asymmetric membrane to immobilize microorganisms for certain biological processes that use soluble carbon sources. However, the adaptation and use of such membranes for the anaerobic bioconversion of syngas to liquids has not been shown in the past.

Existing bioreactors are either small scale, unsuitable for large scale manufacturing processes, or custom designed, increasing manufacturing and installation costs. The costs of membrane housings and piping can be a significant addition to the cost of the membrane itself. Bioreactors have been unable to take advantage of standardized configurations and hardware that would improve the plant economics.

It would be desirable to have a stacked array bioreactor for conversion of syngas components to liquid products that would overcome the above disadvantages.

SUMMARY OF THE INVENTION

It has been found that contacting syngas components such as CO or a mixture of $CO_2$ and $H_2$ with a surface of a membrane that contains a biolayer of microorganisms and permeating liquid to and from the opposite side of the membrane will provide a stable system for producing liquid products such as ethanol, butanol, hexanol, and other chemicals. The membrane has an asymmetric construction that provides a porous side, referred to herein as a biolayer that provides pores to promote and control the growth of microorganism colonies therein while also exposing a surface over which to directly feed the microorganisms with syngas. Simultaneously another layer of the asymmetric membrane having less permeability than the biolayer, herein referred to as a hydration layer, permeates liquid from the opposite side of the asymmetric membrane. Accordingly, this invention is a membrane supported bioreactor system for conversion of syngas components such as CO, $CO_2$, and $H_2$ to liquid fuels and chemicals by anaerobic microorganisms supported on or within the surface of membrane and in direct contact with the gas phase syngas components. The liquid products produced in the biolayer on the membrane's gas contact side pass through the membrane and into a liquid stream that recovers the desired liquid products while also supplying nutrients to the biolayer in the reverse direction of liquid product flow.

One embodiment of this invention includes a modular membrane bioreactor for anaerobic conversion of gas into liquid products including a plurality of axially stacked membrane modules having a plurality of hollow fibers packed across a transverse cross sectional area of the membrane module in a direction transverse to a longitudinal axis of the membrane module, each of the plurality of hollow fibers having an asymmetric membrane wall defining a porous biolayer about an outer surface of the membrane wall and a less permeable hydration layer around the hollow fiber lumen; a membrane vessel having an interior sealed from ambient atmosphere for retaining the membrane modules surrounded by a process gas in communication about the outer surface of the hollow fiber wall for formation of a biolayer by interaction of microorganisms with the process gas and for production of a liquid product, the membrane vessel having a vessel cross sectional area perpendicular to the longitudinal axis of the membrane vessel of no more than 1.5 times the transverse cross sectional area of the membrane module; a liquid supply conduit for communicating a process liquid with the hollow fiber lumens of the hollow fibers for permeation of water and nutrients to the biolayer and permeation of liquid product from the biolayer into admixture with the process liquid; a liquid recovery conduit operably connected to the hollow fiber lumens for recovering the process liquid containing the liquid product that permeates from the biolayer across at least a portion of the hollow fiber wall; and a gas supply conduit for supplying the process gas to the interior of the membrane vessel.

Another embodiment of this invention includes a modular membrane bioreactor for anaerobic conversion of syngas into liquid products including a plurality of membrane modules stacked in an axial direction, each membrane module having a plurality of hollow fibers, each of the plurality of hollow fibers comprising an asymmetric membrane wall defining biopores on an outer layer of the hollow fiber for retaining a porous biolayer about an outer surface of a hollow fiber wall of the hollow fiber and a less permeable hydration layer around a hollow fiber lumen of the hollow fiber; a membrane vessel for retaining the membrane modules surrounded by a process gas containing at least one of CO or a mixture of $CO_2$ and $H_2$ at a pressure above atmospheric pressure for the formation of the porous biolayer containing microorganisms selected from the group consisting of *Clostridium ragsdalei*, *Butyribacterium methylotrophicum*, *Clostridium ljungdahlii*,

*Clostridium carboxidivorans*, and combinations thereof about the outer surface of the hollow fiber wall and for the production of a liquid product selected from the group consisting of ethanol, n-butanol, hexanol, acetic acid, butyric acid, and combinations thereof by interaction of microorganisms with the process gas and process liquid that permeates across the hollow fiber wall; a liquid supply conduit for serially communicating a process liquid with the hollow fiber lumens of the hollow fibers for permeation of water and nutrients to the biolayer and permeation of the liquid product from the biolayer into admixture with the process liquid; a liquid recovery conduit in communication with the hollow fiber lumens to recover the process liquid containing the liquid product from the membrane vessel; a gas supply conduit for supplying the process gas containing at least one of CO or a mixture of $CO_2$ and $H_2$ to the interior of the membrane vessel; and a product recovery system operably connected to receive the process liquid from the liquid recovery conduit, to separate the liquid product from the process liquid, and to return the process liquid to the membrane vessel.

Yet another embodiment of this invention includes a bioreaction method including retaining a process gas in a membrane vessel under anaerobic conditions; maintaining multiple membrane modules in the process gas as a stacked arrangement, the membrane modules having a plurality of hollow fibers, each of the plurality of hollow fibers having a hollow fiber wall defining a hollow fiber lumen and an outer surface; growing a biolayer containing microorganisms about the outer surface of the hollow fibers by using at least a portion of the process gas as feed to the microorganisms; and passing a process liquid into the hollow fiber lumens and circulating process liquid from the hollow fiber lumens across the hollow fiber walls to interact with the biolayer and generate a liquid product that mixes with the process liquid.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE INVENTION

Figure 1:
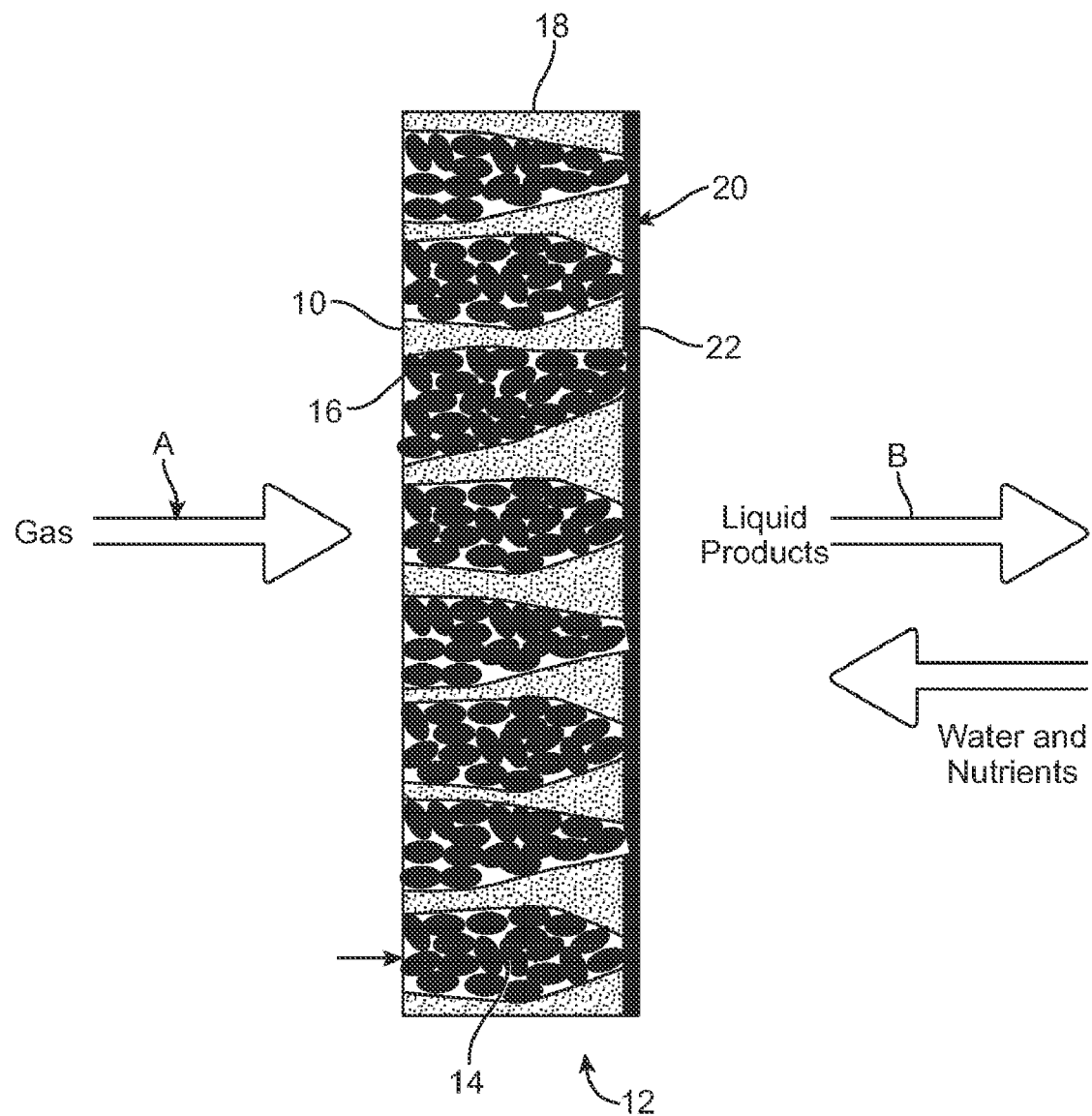
FIG. 1 is a schematic drawing of a cross-section of an asymmetric membrane with gas stream in contact with a biolayer that retains microorganisms therein and a hydration layer in the form of a skin in contact with liquid.

This invention is further described in the context of a bioconversion process for the production of ethanol from CO and/or mixtures of $H_2/CO_2$ using modules containing hollow fiber membranes. The description of the invention in a particular context does not restrict its application or claim coverage from other process applications that meet the criteria for its use.

This invention finds ready application to the production of acetic acid, ethanol, and other products from a feed gas stream. Such conversions using microorganisms are well known. For example, in a recent book concise description of biochemical pathways and energetics of such bioconversions have been summarized in "Electron Transport System in Acetogens," by A. Das and L. G. Ljungdahl, and "Diverse Physiologic Potential of Acetogens," by H. L. Drake and K. Kusel, appearing respectively as Chapters 14 and 13 of *Biochemistry and Physiology of Anaerobic Bacteria*, L. G. Ljungdahl, Ed., Springer (2003). Any suitable microorganisms that have the ability to convert the syngas components of CO, $H_2$, $CO_2$, individually or in combination with each other, or with other components that are typically present in syngas, may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC No. BAA-624; and U.S. patent application Ser. No. 11/514,385, filed Aug. 31, 2006, entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms include the anaerobic bacteria *Butyribacterium methylotrophicum*, having the identifying characteristics of ATCC 33266 which can be adapted to CO and used. This enables the production of n-butanol as well as butyric acid as taught in the references: "Evidence for Production of n-Butanol from Carbon Monoxide by *Butyribacterium methylotrophicum*," in *Journal of Fermentation and Bioengineering*, vol. 72, 1991, pp. 58-60; and "Production of Butanol and Ethanol from Synthesis Gas via Fermentation," in FUEL, vol. 70, May 1991, pp. 615-619. Other suitable microorganisms include *Clostridium ljungdahlii*, with strains having the identifying characteristics of ATCC 49587 as disclosed in U.S. Pat. No. 5,173,429 entitled "Biological Production of Ethanol from Waste Gases with *Clostridium ljungdahlii*," and ATCC 55988 and 55989 as disclosed in U.S. Pat. No. 6,136,577 entitled "Biological Production of Ethanol from Waste Gases with *Clostridium ljungdahlii*." This will enable the production of ethanol as well as acetic acid. All of the above references are incorporated by reference herein in their entirety.

The microorganisms found suitable thus far for bioconversion for this invention require anaerobic growth conditions. Therefore, the bioconversion system employs suitable control and sealing methods to limit the introduction of oxygen into the system. Since the microorganisms contact the liquid that circulates through the bioreactor system, a suitable redox potential is maintained and monitored to insure anaerobic conditions. Anaerobic conditions in the liquid volume are usually defined as having a redox potential of less than −200 mV and preferably a redox potential in the range of from −300 to −500 mV. To further minimize exposure of the microorganisms to oxygen, the feed gas will preferably have an oxygen concentration of less than 1000 ppm, more preferably less than 100 ppm, and even more preferably less than 10 ppm.

The invention uses asymmetric membranes having a porous layer and a less permeable layer. The porous layer, referred to as the biolayer, can be any material suitable for the formation of the biopores and the transport of liquid to and away from the microorganisms in the biopores. The less porous layer, referred to as the hydration layer, controls the transport of the fermentation liquid to and from the biolayer for nourishing the microorganisms and maintains effluent products at desired concentrations. The biolayer and hydration layer are described as single layers, but either or both can include several layers.

The asymmetric membrane also requires material that provides support to the membrane structure and occludes the internal end of the biopores to prevent microorganisms and other biological material from passing into the fermentation liquid. The asymmetric membrane can contain additional layers for internal support and formation of the biopores or the biolayer and/or hydration layer may serve these functions as well. Any additional layers can permit direct contact of syngas with the microorganisms in the biopores and the permeation of liquid into the biolayer.

The biolayer defines the biopores for retaining the microorganisms in direct contact with the syngas. The biopores require an effective diameter of at least 1 µm over at least a portion of its length. The term effective diameter refers to the open cross-sectional area of a regularly shaped pore that would provide the same cross-sectional area. The pores need not have a uniform cross-section and biopores having an effective diameter of 1 µm over at least a third of its length are suitable. The biopores in the biolayer of the membrane usually have an effective diameter substantially greater than 1 µm, preferably in the range of 2 to 100 µm, and most preferably in the range of 5 to 50 µm. Typical depths of the biopores range from 50 to 500 µm which generally corresponds to the thickness of the biolayer.

The hydration layer can have restricted liquid permeability with respect to the biolayer. The restricted permeability prevents excessive fermentation liquid from migrating into the biolayer during normal operation of the system and interfering with contact between the gas and microorganisms. In most cases, the hydration layer is a higher density material than the biolayer that restricts liquid flow while also occluding the internal end of the biopores to block migration of the microorganisms into the fermentation liquid.

Particularly suitable forms of asymmetric membranes are porous membranes with a tight (i.e., having small pores) thin "skin" on one surface of the membrane that provides the hydration layer and a relatively open support structure underneath the skin that provides the biolayer and defines the biopores. The skin will typically comprise a semi-permeable layer having a thickness of from 0.5 to 10 µm. The skinned asymmetric membrane can include an "integrally skinned" membrane prepared by using phase inversion of one polymer or a composite membrane, where a thin layer of a certain material is formed on top of a porous sublayer of a same or different material. General description of asymmetric membranes and methods of their preparation can be found in the literature (e.g., M. Cheryn, *Ultrafiltration and Microfiltration Handbook*, Technomics Publishing Company, Lancaster, Pa, 1998; and M. Mulder, *Basic Principles of Membrane Technology*, $2^{nd}$ Edition, Kluwer Academic Publishers, Norwell, Mass, 1996).

A suitable skin layer has a pore size that is smaller than the size of microbial cells to prevent the cells from passing through the membrane skin but the opposite surface of the membrane has large openings that allow cells to enter and leave the biopores of the membrane wall. Typically, the pore size of the skin layer is less than 0.5 µm, preferably less than 0.25 µm, and most preferably in the ultrafiltration range of nominal MWCO of 10 to 300 kDa and more preferably in the range of 10 to 100 kDa.

Several asymmetric ultrafiltration membranes are available from Millipore Corporation (Bedford, Mass.), including but not limited to the Amicon Membranes and the Ultracel PLC Membranes. The Amicon Membranes are made of polyethersulfone and with a range of a nominal MWCO, for example a nominal MWCO of 30 kDa for Amicon PM30. The Ultracel PLC Membranes, which are composite membranes made from casting the regenerated cellulose membrane onto a microporous polyethylene substrate, are available in the pore size range from 5 kDa (PLCCC) to 1000 kDa (PLCXK). Additional examples of asymmetric membranes are the MMM-Asymmetric Super-Micron Membranes and BTS Highly Asymmetric Membranes, both available from Pall Corporation (East Hills, N.Y.). The MMM-Asymmetric Membranes, available in pore size range from 0.1 to 20.0 µm, are made of polysulfone and polyvinylpyrrolidone. The BTS Highly Asymmetric Membranes, available in pore size range from 0.05 to 0.80 µm, are cast of polysulfone with a "cut off" layer of about 10 µm and a total thickness of about 120 µm.

Hollow fiber membrane modules containing asymmetric ultrafiltration membranes are commercially available from a number of membrane manufacturers. For example, the Kros-Flo® Max Module Model KM5S-800-01N from Spectrum Laboratories (Rancho Dominguez, Calif.) has 22.0 $m^2$ membrane surface area of asymmetric polysufone hollow fiber membranes with 0.5 mm fiber inner diameter, a tight skin on the lumen side, and a pore rating of 50 kDa. ROMICON® polysulfone hollow fiber membranes available from Koch Membrane Systems (Wilmington, Mass.) are also asymmetric with the tight skin on the lumen side. ROMICON cartridge Model HF-97-43-PM50 is a 6-inch module containing fibers of 1.1 mm inner diameter and 50 kDa nominal MWC at 9.0 $m^2$ total membrane surface area.

Membranes of the various geometries and compositions described above may be used in arrangements of unitary arrays or assemblies of varied composition in the systems of this invention. Any suitable potting technique can be used to collect and provide the necessary assembly of individual membrane elements. In such membranes the gas and liquid can be brought into direct and intimate contact at the gas contact surface of the biolayer. Liquid is passed in the liquid side of the membranes via pumping, stirring, or similar means to remove the ethanol and other soluble products formed; the products are recovered via a variety of suitable methods.

The syngas flows through the gas chamber or channels of the bioreactor system continuously or intermittently. The feed gas pressure is in the range of 1 to 1000 psig, preferably 5 to 400 psig, and most preferably 10 to 200 psig. The differential pressure between the liquid and gas phases is managed in a manner that the membrane integrity is not compromised (e.g., the burst strength of the membrane is not exceeded) and the desired gas-liquid interface phase is maintained.

The gas side pressure is normally slightly higher than the liquid pressure to prevent convective liquid flow from the hydration layer (liquid) side to the open surface (gas) of the gas contacting side. The higher pressure also avoids formation of a liquid layer at the cell/gas interface, which would impede gas transfer to the cells.

When the feed syngas contains moisture, condensation of water can occur at the microorganism/gas interface as consumption of syngas results in supersaturation of water. This condensed water leaves the cell/gas interface by dripping to the bottom of the bioreactor due to gravity as well as by convective flow through the membrane due to the slightly higher pressure of the gas.

FIG. 1 is a schematic drawing showing a cross-section of an asymmetric membrane with a gas stream in contact with a biolayer that retains microorganisms therein and a hydration layer in the form of a skin in contact with liquid. An asymmetric membrane, suitable for permeation of the fermentation liquid, provides separation between the liquid phase and feed gas comprising at least one of CO or a mixture of $H_2$ and $CO_2$. FIG. 1 shows detail of the membrane configuration and interface in the operation of a representative bioreactor system. FIG. 1 depicts a cross-section of a single membrane element with a syngas stream A flowing to the gas contacting side 10 of the asymmetric membrane 12. The syngas components directly contact the microorganisms 14 contained in biopores 16. An anaerobic acetogenic bacteria, such as *Clostridium ragsdaeli* having all of the identifying characteristics of ATCC No. BAA-622, is maintained in the biopores 16 and is supplied with the fermentation liquid by permeation through the biolayer 18. The fermentation liquid circulates on the opposite side of the syngas stream A and permeates through a hydration layer formed as skin 20 on the inner surface of biolayer 18. Direct contact of the skin 20 with the biolayer 18 transfers the fermentation liquid to the biopores 16. The surfaces of biolayer 18 that contact the microorganisms and gas stream provide equilibrium partitioning across the asymmetric membrane to keep the liquid and gas phases separated from each other. The pores in the skin 20 are much smaller than the width of the microorganisms retained in the biopores 16 so that the skin 20 occludes the inner end of the biopores 16 and prevents the microorganisms from passing through the skin 20 and to liquid contacting surface 22. As a result, the microorganisms 14 preferentially stay within the biopores 16 to gain metabolic energy by converting CO and $H_2/CO_2$ thereby growing and sustaining themselves within the biopores 16. A portion of liquid B is withdrawn and separated to recover the desired products from the fermentation liquid.

To load the asymmetric membrane with microorganisms, the biolayer is first inoculated with microorganisms, followed by further cell growth to reach the desired cell loading density. To inoculate the biolayer, an aqueous solution containing microorganisms is introduced to the gas contacting side of the asymmetric membrane, and then the solution is slowly filtered through the biolayer and hydration layer by applying a slight trans-membrane pressure, creating a microorganism-free filtrate through the hydration layer and entrapping cells within the biopores of the biolayer. The microorganism-containing membrane is incubated for further microorganism growth, by contacting the membrane with a liquid solution containing nutrients and carbon source suitable for microorganism growth. Alternatively, the membrane can be incubated using a syngas and a liquid solution containing nutrients.

Figure 2:
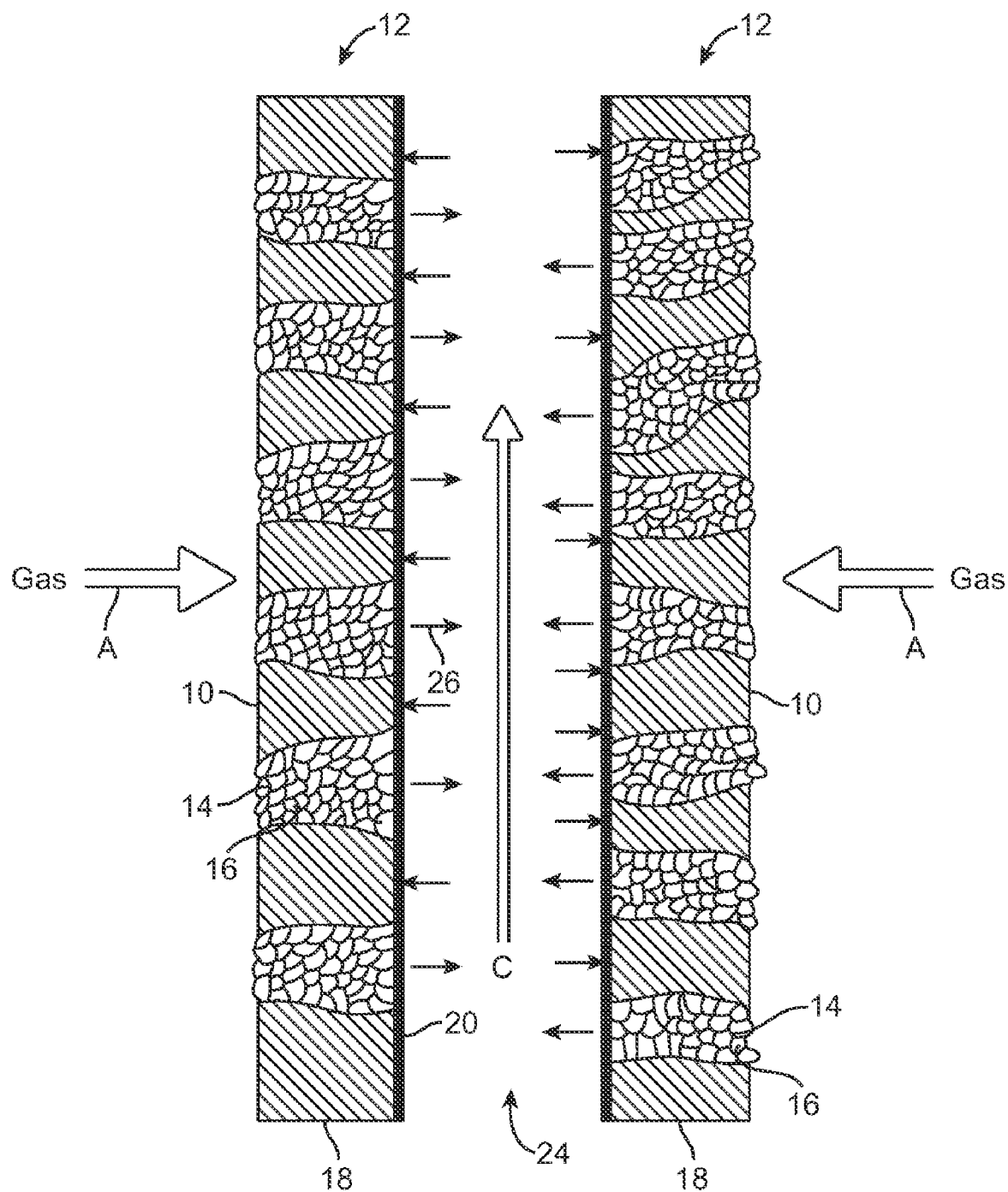
FIG. 2 is a schematic drawing of a central passage formed by two membranes of the type shown in FIG. 1 with a gas stream contacting the outer wall and liquid contacting the inner walls.
Figure 3:
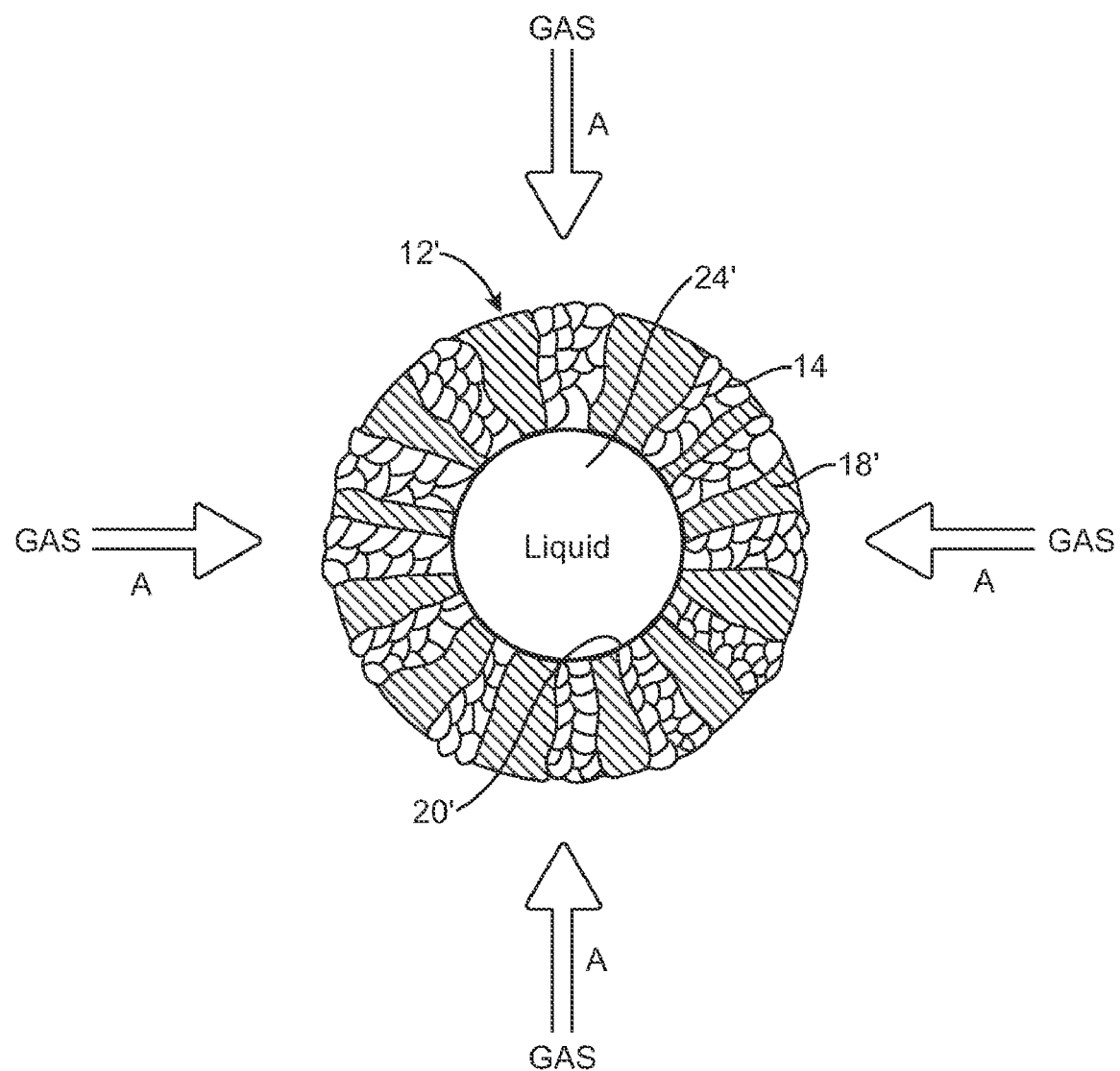
FIG. 3 is a schematic drawing of a transverse cross-section of the asymmetric membrane of FIG. 1 made into a hollow fiber with the biolayer on the outside and the hydration layer on the inside.

FIGS. 2 & 3 show various configurations of asymmetric membranes with microorganisms present within biopores of the biolayers.

FIG. 2, in which like elements share like reference numbers with FIG. 1, is a schematic drawing showing a central passage formed by two membranes of the type shown in FIG. 1 with a gas stream contacting the outer wall and liquid contacting the inner walls. Two asymmetric membranes 12 border a central liquid channel 24 through which a fermentation liquid circulates in the direction of stream C. The asymmetric membranes 12 on each side of liquid channel 24 function in a similar manner to that described for the single membrane element of FIG. 1. Syngas flows across gas contacting side 10 into contact with the microorganisms 14 and fermentation products pass out the skin 20 in the direction of arrows 26. The arrangement of FIG. 2 can use a flat sheet configuration or a tubular configuration and be particularly useful for good flow control and distribution on the liquid side.

FIG. 3 is a schematic drawing showing a transverse cross-section of the asymmetric membrane of FIG. 1 made into a hollow fiber with the biolayer on the outside and the hydration layer on the inside. FIG. 3 shows a special case of FIG. 2 wherein the asymmetric membrane 12' wraps around in continuous form to provide a tubular membrane with a central liquid channel 24'. In this case the syngas stream A flows radially inward into contact with the microorganisms 14 contained within an annular biolayer 18'. The skin 20' covers the inner surface of the biolayer 18' and controls the permeation of liquid across biolayer 18'.

In most operations the membrane arrangements will benefit from occasional purging or flushing of the biopores and gas contacting surfaces. For this purpose, periodically during syngas fermentation, the liquid pressure can be increased for a short time to become slightly higher than the gas pressure to create a liquid flow through the membrane to purge some accumulated dead microorganisms or biopolymers from the biopores and from the gas contacting surface. This water is collected from the gas stream side of the bioreactor. Optionally, this water stream may be treated for removal of suspended solids and recirculated to the bioreactor system.

It can also be desirable to clean the biopores and biolayer. This process begins with substantially removing the immobilized cells and the cleaning the asymmetric membrane. The gas supply is stopped, and the membrane is cleaned with cleaning solutions in manners similar to typical cleaning of microfiltration and ultrafiltration membranes. For example, the asymmetric membrane can be first soaked in a cleaning solution from both the sides, e.g., the biolayer and hydration layer. The cleaning solution is formulated or selected to facilitate solubilization of microorganism and biopolymers. One of such solutions is an aqueous solution containing 2% NaCl and 0.4% NaOH, but many other formulations have been used for membrane cleaning, including some containing surfactants and hydrolytic enzymes. After soaking, the cleaning solution is circulated and a positive trans-membrane pressure is applied from the hydration layer side to create a convective flow through the membrane and flush microorganism and biopolymers out through the gas contacting surface of the biolayer. The soaking-filtration procedures can be repeated as needed, and different cleaning solutions can be used. After membrane cleaning, the membrane can be used for loading and growing new cells for syngas fermentation again.

Finally, the asymmetric membrane may benefit from a periodic surge of liquid from channel 24 toward the biopores followed by backflush of the liquid from the biopores to channel 24. This periodic laving of the liquid enhances the delivery of nutrients to the microorganisms and the recovery of liquid products from the biopores. The laying cycle differs significantly from the previously described purging since the laving cycle will occur more often than purging and seeks to avoid any discharge of liquid from the biopores. Therefore laving, like purging occurs by temporarily increasing the relative liquid pressure to gas pressure across the membrane but to a lesser degree than effected during the purge cycle. U.S. Patent Publication 20100105116 contains additional information related to laving and is incorporated herein by reference in its entirety.

Figure 4:
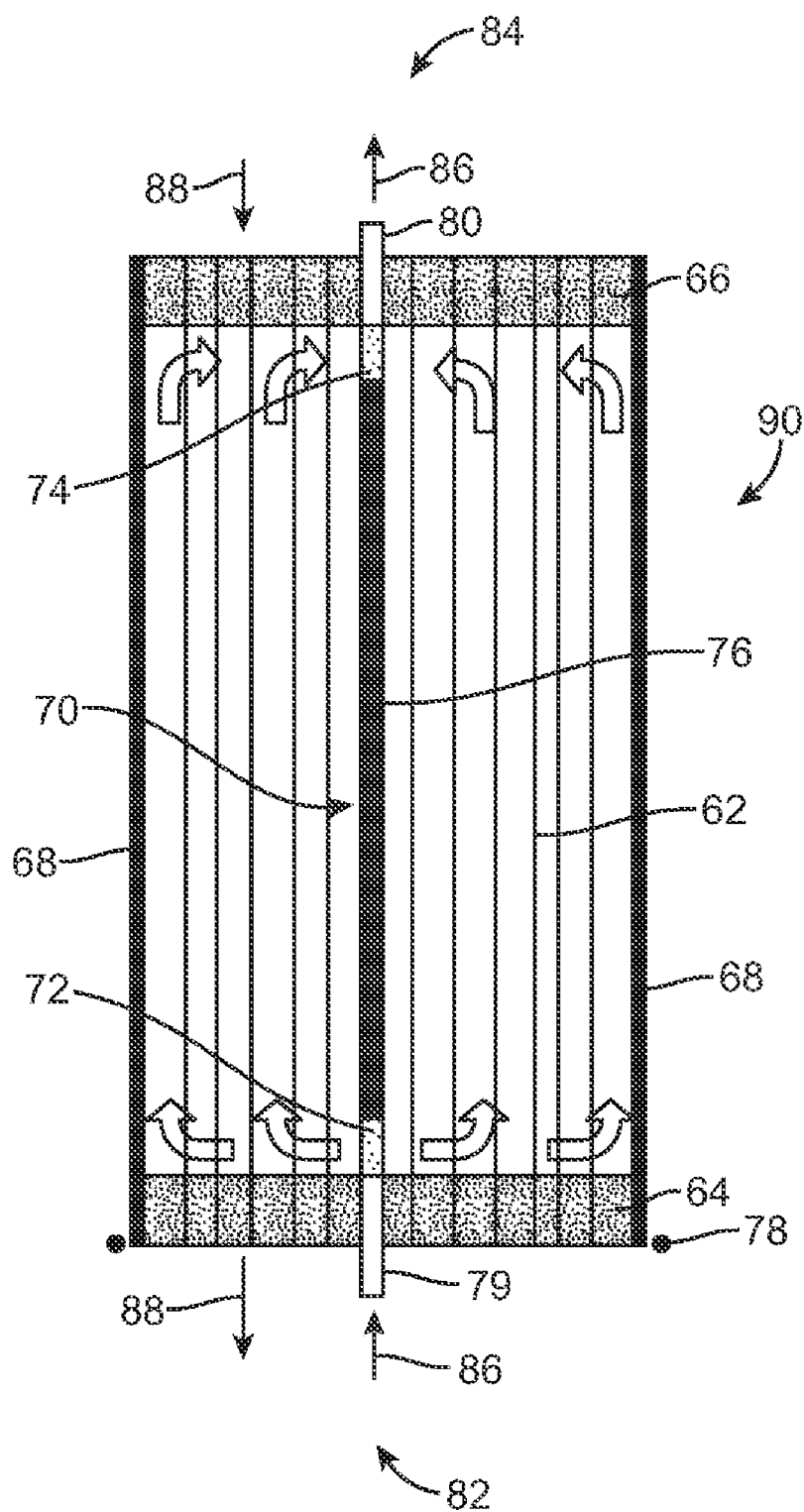
FIG. 4 is a schematic drawing of a two-headed membrane module for use in a bioreactor system with gas and liquid circulation.

FIG. 4 is a schematic drawing of a two-headed membrane module for use in a bioreactor system with gas and liquid circulation. Each membrane module provides a large surface area of asymmetric hydrophilic membranes in the form of hollow fibers. The membrane vessel can be round, square, rectangular or any other suitable shape In the arrangement and method of this invention, process liquid fills the hollow fiber lumens, while a biolayer and process gas are on the shell side of the hollow fibers. A number of the membrane modules can be located in a sealed membrane vessel containing process gas, so that a very large total membrane surface area can be achieved with a small number of membrane vessels, simplifying plant design and reducing costs. Those skilled in the art will appreciate that the membrane modules can have any cross section as desired for a particular purpose, such as round, rectangular, square, or any other cross section that accommodates the shape of the membrane vessel.

In this arrangement, the membrane module 90 includes a number of hollow fibers 62, each having a gas permeable, asymmetric hollow fiber wall defining a hollow fiber lumen and an outer surface. The asymmetric membrane walls define a porous layer of biopores about the outer surface of the membrane wall and a less permeable hydration layer around the hollow fiber lumen, and the porous biopores open to the outer surface of the hollow fibers and contain the biolayer. A process liquid is disposed in the hollow fiber lumens and a biolayer is disposed on or within the outer surface of the hollow fibers. Process gas passes through the hollow fiber wall to interact with the biolayer and generate a liquid product that mixes with the process liquid. Process liquid passes through the hollow fiber wall in the opposite direction to provide water and nutrients to the biolayer. A bottom potted end 64 is operably connected to one end of the hollow fibers 62 and a top potted end 66 is operably connected to the other end of the hollow fibers 62, so that the process liquid can flow through one of the potted ends, through the hollow fiber lumens, and through the other one of the potted ends. The hollow fibers 62 can be potted to the bottom potted end 64 and the top potted end 66 with an epoxy or the like. A number of support rods 68 connect the bottom potted end 64 and the top potted end 66 to provide mechanical strength to the membrane module, which must withstand forces caused by weight of the hollow fibers and the biolayer, weight of the process liquid within the hollow fiber lumens, membrane module handling, and the like. The hollow fibers can be oriented vertically or horizontally. The two headed arrangement provides support to the hollow fibers and facilitates use in a horizontal as well as vertical orientation.

The length of the hollow fibers 62 can be greater than the distance between the bottom potted end 64 and the top potted end 66 to give the hollow fibers 62 some slack and freedom to move. In one embodiment, the length of the hollow fibers have a length equal to 1.015 to 1.15 times the distance between the bottom potted end 64 and the top potted end 66. In another embodiment, the length of the hollow fibers have a length of equal to 1.01 to 1.15 times the distance between the bottom potted end 64 and the top potted end 66. A mechanical seal 78, such as an O-ring or the like, located around the membrane module helps secure and stabilize the membrane module in the membrane vessel. The mechanical seal 78 also prevents process gas or process liquid from bypassing the membrane module. In one embodiment, the mechanical seal is an intermittent seal, which is defined herein as a seal with gaps along the length, leaving spaces through which liquid can flow. In another embodiment, the mechanical seal is a porous seal, which is defined herein as a seal made of a porous material through which liquid can flow. Intermittent seals and/or porous seals can be used to drain condensation and leakage from the process gas side of the membrane module and can be used in startup and maintenance operations. The mechanical seal can also provide lateral support to the membrane module. In yet another embodiment, the mechanical seal can be omitted.

A tube 70 runs the length of the membrane module between the bottom potted end 64 and the top potted end 66, passing through both the bottom potted end 64 and the top potted end 66. The tube 70 includes a bottom perforated section 72 near the bottom potted end 64, a top perforated section 74 near the top potted end 66, and a blocked section 76 between the bottom perforated section 72 and the top perforated section 74. In this arrangement as indicated by the hollow arrows, process gas in the tube 70 passes through the bottom potted end 64 and out the bottom perforated section 72, along the outer surfaces of the hollow fibers 62, in the top perforated section 74 and through the top potted end 66. The middle section 76 of the tube 70 is blocked, so that the flow of the process gas follows the outer surfaces of the hollow fibers 62. The perforated sections of the tube 70 allow the process gas to distribute radially about the hollow fibers 62 once the process gas passes through the potted end. The tube primarily functions to distribute and collect gas from the hollow fibers 62 about a central area of the potted ends 64, 66 and can also serve as a central support between the potted ends. When central support is not needed, the continuous tube may be replaced with simple distributors and collectors.

In the arrangement depicted by FIG. 4, the membrane modules are countercurrent flow membrane modules: the process gas enters the bottom of the membrane module and exits the top, and the process liquid enters the top of the membrane module and exits the bottom. Those skilled in the art will appreciate that the membrane modules can be countercurrent flow or cocurrent flow, with the process gas or process liquid entering the top or the bottom of the membrane module as desired for a particular application.

Bottom gas connection 79 and top gas connection 80 are connected to or part of the tube 70 where the tube 70 passes through the bottom potted end 64 and the top potted end 66, respectively. The gas connections 79, 80 can be attached to piping that passes out of the membrane vessel or can be attached to gas connections of adjacent membrane modules when a number of membrane modules are connected in series within a membrane vessel. The hollow fibers 62 pass through the potted ends 64, 66, so that the hollow fiber lumens are open to bottom space 82 and top space 84. The bottom space 82 and top space 84 can be in communication with piping that passes out of the membrane vessel or adjacent membrane modules when a number of membrane modules are connected in series within a membrane vessel. In this arrangement, process gas enters the membrane module 90 at the bottom gas connection 79 and exits the membrane module 90 at the top gas connection 80, as indicated by the arrows 86. Also in this arrangement, process liquid enters the membrane module 90 at the top potted end 66 and exits the membrane module 90 at the bottom potted end 64, as indicated by the arrows 88.

Figure 5:
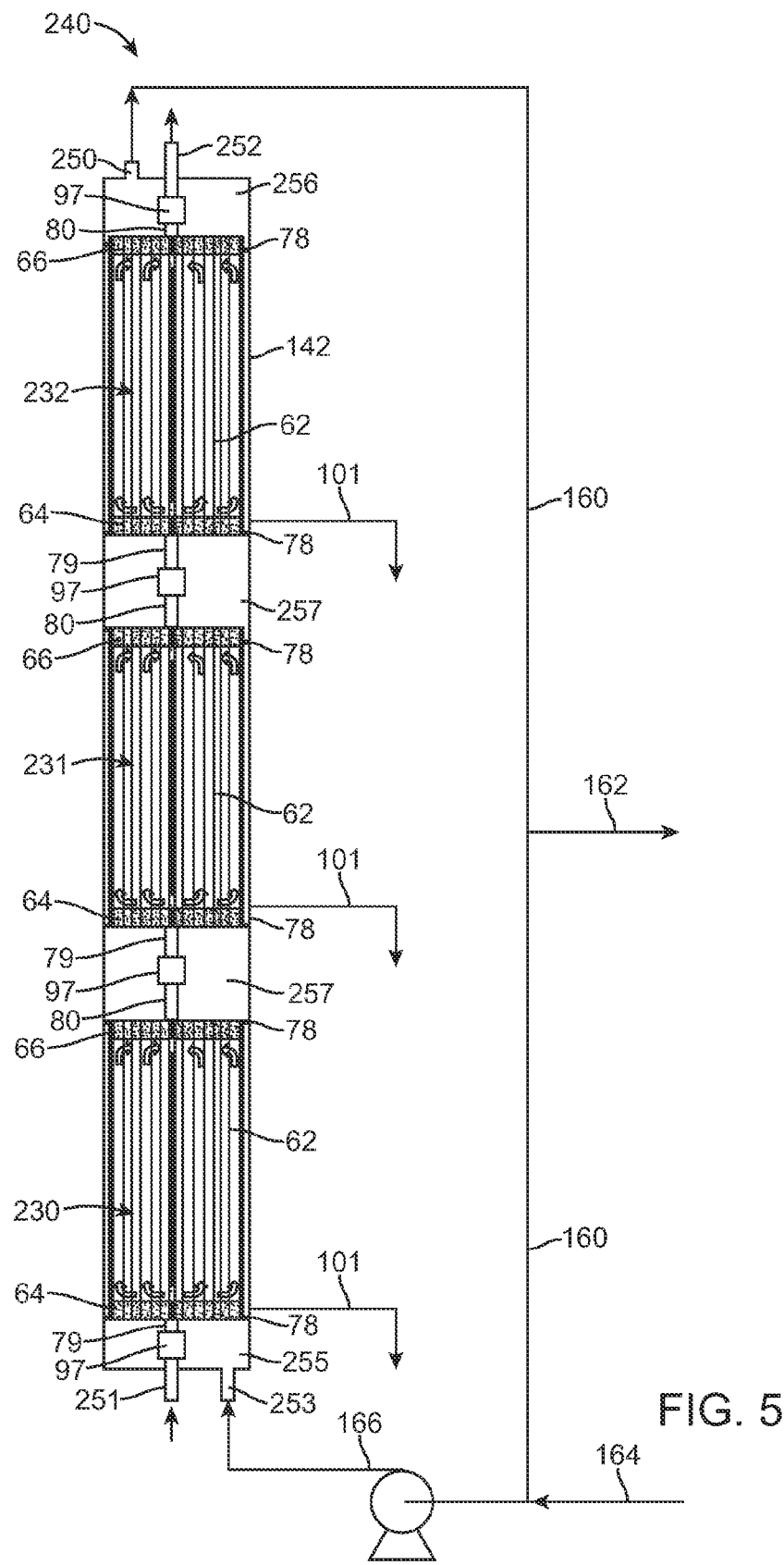
FIG. 5 is a schematic drawing of a bioreactor system with a plurality of the two-headed membrane modules of FIG. 4 connected in series.

FIG. 5, in which like elements share like reference numbers with FIG. 4, is a schematic drawing of a bioreactor system with the two-headed membrane modules of FIG. 4 connected in series. In this embodiment, the bioreactor 240 includes a number of axially stacked membrane modules 230, 231, 232, which are two-headed membrane modules as described further for FIG. 4. Referring to FIG. 5, a number of hollow fibers are packed across a transverse cross sectional area of the membrane module in a direction transverse to a longitudinal axis of the membrane module, which is the axis extending from the top to the bottom of the membrane vessel 142. The membrane modules 230, 231, 232 are connected in series between the liquid inlet plenum 255 and the liquid outlet plenum 256, with liquid intermediate plenums 257 between adjacent membrane modules, and connectors 97 joining the top gas connection 80 of one membrane module to the bottom gas connection 79 of the adjacent membrane module. The connectors 97 also connect the bottom gas connection 79 of the membrane module 230 to the gas supply conduit 251 and the top gas connection 80 of the membrane module 232 to the gas recovery conduit 252. The gas supply conduit 251 supplies the process gas to the interior of the membrane vessel 142.

The membrane vessel 142 has an interior sealed from ambient atmosphere for retaining the membrane modules 230, 231, 232 surrounded by process gas in communication about the outer surface of the hollow fiber walls for formation of a biolayer by interaction of microorganisms with the process gas and for production of a liquid product. The membrane vessel 142 has a vessel cross sectional area perpendicular to the longitudinal axis of the membrane vessel of no more than 1.5 times the transverse cross sectional area of the membrane module 230, 231, 232. In one embodiment, the membrane vessel 142 is adapted to contain a pressure in the range between 15 and 150 psig.

The membrane modules 230, 231, 232 have top potted ends 66 and bottom potted ends 64. The top potted end 66 is connected to one end of the hollow fibers 62 and the bottom potted end 64 is connected to the other end of the hollow fibers 62 to allow the process liquid to flow through the hollow fiber lumens from the bottom potted end 64 to the top potted end 66. The process liquid from the hollow fiber lumens of one two-headed membrane module flows through the hollow fiber lumens of the other two-headed membrane modules and the process gas about the outer surface of the hollow fibers of one two-headed membrane module flows about the outer surface of the hollow fibers of the other two-headed membrane modules. That is, the process liquid and the process gas flow through all the membrane modules 230, 231, 232. In one embodiment, the relative flow between the process gas and process liquid is concurrent flow as illustrated. In another embodiment, the relative flow between the process gas and process liquid is countercurrent flow. In one embodiment, the hollow fiber lumens extend vertically and the process liquid flows in a principally downward direction through the hollow fiber lumens.

A process gas, such as syngas or the like, enters the membrane vessel 142 through gas supply conduit 251 and enters the bottom membrane module 230 through its bottom gas connection 79. The process gas passes about the outer surface of the hollow fibers 62 of bottom membrane module 230, exits the bottom membrane module 230 through its top gas connection 80 and enters the adjacent membrane module 231 through its bottom gas connection 79. The process gas continues through the membrane modules until reaching the top membrane module 232 and exiting the membrane vessel 142 through the gas recovery conduit 252. In one embodiment, the gas recovery conduit can be closed to maximize gas utilization efficiency.

Process liquid enters the membrane vessel 142 through liquid inlet 253 and enters the liquid inlet plenum 255 between the membrane vessel 142 and the bottom membrane module 230. The process liquid is distributed from the liquid inlet plenum 255 into the hollow fiber lumen of each hollow fiber 62 through the bottom potted end 64. As the process liquid flows along the length of the hollow fibers 62, process liquid and process gas interact with the biolayer on the outer surface of the hollow fibers 62 to generate liquid product, which mixes into the process liquid. The process liquid exits the bottom membrane module 230 through its top potted end 66 and enters the liquid intermediate plenum 257 between the bottom membrane module 230 and the adjacent membrane module 231. The process liquid continues through the membrane modules until reaching the top membrane module 232 and exiting the membrane vessel 142 through liquid outlet plenum 256 and liquid recovery conduit 250. The liquid recovery conduit 250 is operably connected to the hollow fiber lumens for recovering the process liquid containing the liquid products that permeates from the biolayer across at least a portion of the hollow fiber wall.

The liquid recovery conduit 250 is connected to the membrane vessel 142 to receive the process liquid including liquid product. In one embodiment, the modular membrane bioreactor 240 further includes a product recovery system serving one or more modular membrane bioreactors and operably connected to receive the process liquid from the liquid recovery conduit 250 in a recirculation stream 160. The product recovery system separates the liquid product from the process liquid and returns the process liquid to the membrane vessel 142. At least a portion of the recirculation stream 160 is drawn off as product stream 162 for recovery of the liquid product from the process liquid. The recirculation stream 160 is mixed with a recycle stream 164 including fresh liquid and/or recycled broth, i.e., process liquid at least partially stripped of the liquid product, to form a feed stream 166, which is pumped into the membrane vessel 142 at the liquid supply conduit 253 of the membrane vessel 142. The liquid supply conduit 253 communicates the process liquid with the hollow fiber lumens of the hollow fibers 62 for permeation of water and nutrients to the biolayer and permeation of liquid products from the biolayer into admixture with the process liquid. The feed liquid enters the membrane module 230 after passing through the liquid inlet plenum 255 between the membrane vessel 142 and the membrane module 230.

The connection at the connectors 97 can be made using a number of methods, such as standard pipe-threaded fittings, compression fittings, flanges, sanitary fittings, and the like. The membrane modules can be connected to minimize the size of the liquid intermediate plenums 257. One arrangement using O-rings and sliding seals is described in U.S. Pat. No. 5,851,267, incorporated herein by reference.

The formation of the biolayer containing microorganisms in the various embodiments of this invention can include growing a biolayer supporting microorganisms selected from the group consisting of *Clostridium ragsdalei*, *Butyribacterium methylotrophicum*, *Clostridium ljungdahlii*, *Clostridium carboxidivorans*, and combinations thereof. The anaerobic acetogenic bacteria, *Clostridium carboxidivorans* has all of the identifying characteristics of ATCC No. BAA-624; can be used and this will enable the production of ethanol, n-butanol and acetic acid. The anaerobic bacteria *Butyribacterium methylotrophicum*, has the identifying characteristics of ATCC 33266 and can be adapted to CO use to enable the production of n-butanol as well as butyric acid. The anaerobic bacteria *Clostridium ljungdahlii*, has the identifying characteristics of ATCC 55988 and 55989 can be used to enable the production of ethanol as well as acetic acid.

In this embodiment, the membrane vessel 142 includes shell purge outlets 101 in communication with the interior of the membrane vessel 142 at the bottom of each of the membrane modules 230, 231, 232. Those skilled in the art will appreciate that during certain normal and transitional operation operations it is necessary to drain liquid from the shell side around the outside of the hollow fibers within the membrane vessel 142. During normal operation, condensation and/or leakage can cause liquid to accumulate within the membrane vessel 142. During startup, liquid including suspended microorganisms is filtered from the shell side of the membrane vessel 142 through the hollow fibers 62 to establish the microorganisms within the biopores and the residual liquid drained through the shell purge outlets 101. During purging or flushing of the biopores and gas contacting surfaces, pressure of the process liquid within the hollow fibers 62 is increased so the process liquid flows through the wall of the hollow fibers 62 into the membrane vessel 142 and the residue is drained through the shell purge outlets 101. During cleaning of the biopores and biolayer, cleaning solution can be circulated within the membrane vessel 142 and drained through the shell purge outlets 101.

In other embodiments, the shell purge outlets 101 can be omitted and alternative drain paths provided. The membrane modules when inserted in the membrane vessel 142 can provide at least one continuous flow path for liquid to drain from outside the hollow fibers to a purge outlet. In one embodiment, the top surface of the bottom potted end 64 of each membrane module is contoured, such as a concave shape or the like, so that liquid runs away from the side of the membrane vessel 142 and towards bottom perforated section of the central tube near the bottom potted end 64. The liquid drains through the perforated section, passing from one membrane module to another, and exiting the membrane vessel 142 at the gas supply conduit 251. In this example, the liquid drains in the opposite direction of the gas flow through the membrane modules.

Figure 6:
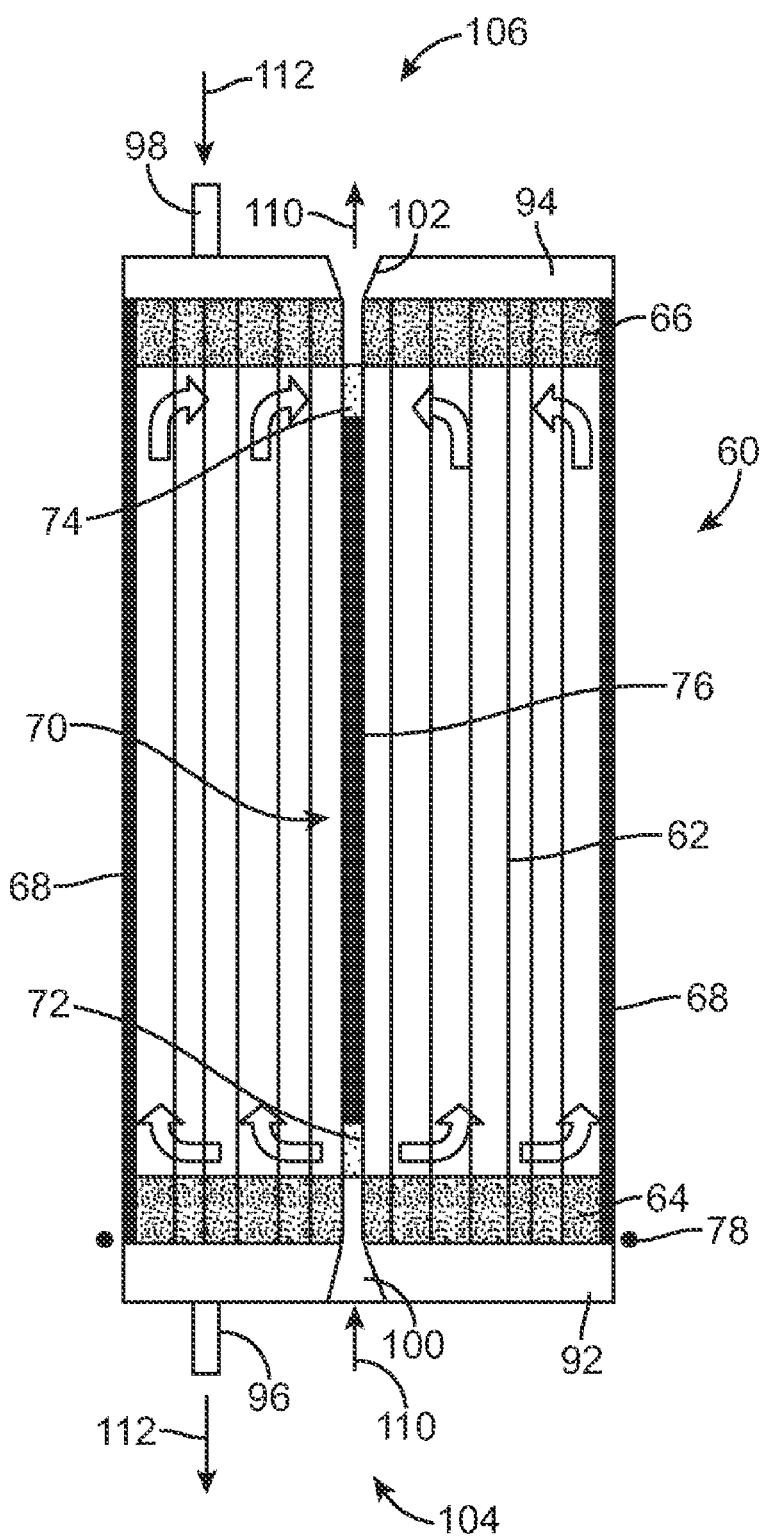
FIG. 6 is a schematic drawing of another two-headed membrane module for use in a bioreactor system with gas and liquid circulation.

FIG. 6, in which like elements share like reference numbers with FIG. 4, is a schematic drawing of another two-headed membrane module for use in a bioreactor system with gas and liquid circulation. As illustrated in FIG. 6, the hollow fibers 62 pass through the potted ends 64, 66, so that the hollow fiber lumens are open to top liquid chamber 94 and bottom liquid chamber 92. The bottom liquid chamber 92 is connected to bottom liquid conduit 96 and the top liquid chamber 94 is connected to the top liquid conduit 98. The liquid conduits 96, 98 can be attached to piping that passes out of the membrane vessel or can be attached to liquid conduits of adjacent membrane modules when a number of membrane modules are connected in series within a membrane vessel. Bottom gas port 100 and top gas port 102 are connected to or part of the tube 70 where the tube 70 passes through the bottom liquid chamber 92 and the top liquid chamber 94, respectively. The bottom gas port 100 and top gas port 102 communicate with bottom space 104 and top space 106, respectively. The gas ports can be shaped as desired to reduce the pressure drop across the gas ports. The bottom space 104 and top space 106 can be in communication with piping that passes out of the membrane vessel or with adjacent membrane modules when a number of membrane modules are connected in series within a membrane vessel. In this arrangement, process gas enters the membrane module 60 at the bottom gas port 100 and exits the membrane module 60 at the top gas port 102, as indicated by the arrows 110. Also in this arrangement, the process liquid enters the membrane module 60 at the top liquid conduit 98 and exits the membrane module 60 at the bottom liquid conduit 96, as indicated by the arrows 112.

Figure 7:
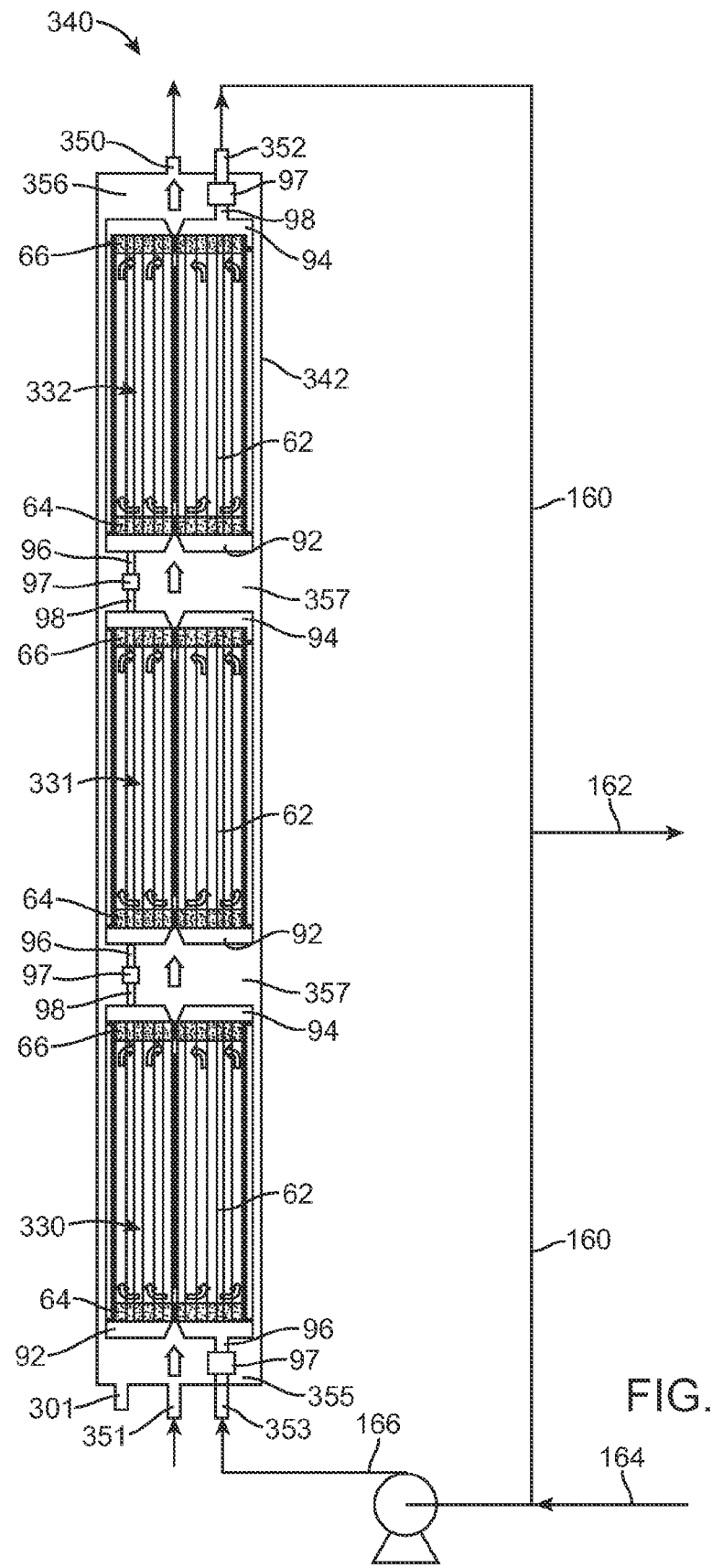
FIG. 7 is a schematic drawing of a bioreactor system with a plurality of the two-headed membrane modules of FIG. 6 connected in series.

FIG. 7, in which like elements share like reference numbers with FIG. 6, is a schematic drawing of a bioreactor system with the two-headed membrane modules of FIG. 6 connected in series. In this embodiment, the bioreactor 340 includes an axial stack of membrane modules 330, 331, 332, which are two-headed membrane modules as described further for FIG. 6. Referring to FIG. 7, the membrane modules 330, 331, 332 are connected in series between the gas inlet plenum 355 and the gas outlet plenum 356, with gas intermediate plenums 357 between adjacent membrane modules, and connectors 97 joining the top liquid conduit 98 of one membrane module to the bottom liquid conduit 96 of the adjacent membrane module. The connectors 97 also connect the bottom liquid conduit 96 of the membrane module 330 to the liquid supply conduit 353 and the top liquid conduit 98 of the membrane module 332 to the liquid recovery conduit 352. The process liquid and the process gas flow through all the membrane modules 330, 331, 332.

A process gas, such as syngas or the like, enters the membrane vessel 342 through gas supply conduit 351 and enters the bottom membrane module 330 through its bottom gas port. The process gas passes about the outer surface of the hollow fibers 62 of bottom membrane module 330, exits the bottom membrane module 330 through its top gas port. The process gas then passes through the gas intermediate plenums 357 and enters the adjacent membrane module 331 through its bottom gas port. The process gas continues through the membrane modules until reaching the top membrane module 332 and exiting the membrane vessel 342 through the gas outlet plenum 356 and the gas recovery conduit 350. In one embodiment, the gas recovery conduit can be closed to maximize gas utilization efficiency. When no mechanical seal is used or the mechanical seal is porous or intermittent, the process gas can also flow around the membrane modules in the spaces between the membrane vessel 342 and the bottom potted end 64, and the membrane vessel 342 and the top potted end 66. A continuous gas flow path can be provided through the membrane vessel 342 from the gas supply conduit 351 to the gas recovery conduit 350: at least one of the membrane vessel 342 and the first and second potted ends of the membrane modules define a portion of the continuous gas flow path. Spacers between the membrane vessel 342 and one or both of the potted ends can be used to stabilize the membrane modules when mechanical seals are not used.

Process liquid enters the membrane vessel 342 through liquid supply conduit 353 and enters the bottom liquid chamber 92 of the membrane module 330. The process liquid is distributed from the bottom liquid chamber 92 into the hollow fiber lumen of each hollow fiber 62 through the bottom potted end 64. As the process liquid flows along the length of the hollow fibers 62, process liquid and process gas interact with the biolayer on the outer surface of the hollow fibers 62 to generate liquid product, which mixes into the process liquid. The process liquid exits the bottom membrane module 330 through its top potted end 66 to the top liquid chamber 94, and then passes through the top liquid conduit 98 to the bottom liquid conduit 96 of the adjacent membrane module 331. The process liquid continues through the membrane modules until reaching the top membrane module 332 and exiting the membrane vessel 342 through its top liquid chamber 94, top liquid conduit 98, and liquid recovery conduit 352.

The liquid recovery conduit 352 is connected to the membrane vessel 342 to receive the process liquid including liquid product. In one embodiment, the modular membrane bioreactor 340 further includes a product recovery system serving one or more modular membrane bioreactors and operably connected to receive the process liquid from the liquid recovery conduit 352 in a recirculation stream 160. At least a portion of the recirculation stream 160 is drawn off as product stream 162 for recovery of the liquid product from the process liquid. The recirculation stream 160 is mixed with a recycle stream 164 including fresh liquid and/or recycled broth, i.e., process liquid at least partially stripped of the liquid product, to form a feed stream 166, which is pumped into the membrane vessel 342 at the liquid supply conduit 353 of the membrane vessel 342. The feed liquid enters the membrane module 330 at the bottom liquid conduit 96.

In this embodiment, the membrane vessel 342 includes a purge outlet 301 in communication with the gas inlet plenum 355. Those skilled in the art will appreciate that during certain normal and transitional operation operations it is necessary to drain liquid from the shell side around the outside of the hollow fibers within the membrane vessel 342. During normal operation, condensation and/or leakage can cause liquid to accumulate within the membrane vessel 342. During startup, liquid including suspended microorganisms is filtered from the shell side of the membrane vessel 342 through the hollow fibers 62 to establish the microorganisms within the biopores and the residual liquid drained through the purge outlet 301. During purging or flushing of the biopores and gas contacting surfaces, pressure of the process liquid within the hollow fibers 62 is increased so the process liquid flows through the wall of the hollow fibers 62 into the membrane vessel 342 and the residue is drained through the purge outlet 301. During cleaning of the biopores and biolayer, cleaning solution can be circulated within the membrane vessel 342 and drained through the purge outlet 301. Liquid can reach the purge outlet 301 through the continuous gas flow path providing a channel for liquid to flow between the membrane vessel 342 and the potted ends 64, 66.

In another embodiment, the top surface of the bottom potted end 64 of each membrane module is contoured, such as a convex shape or the like, so that liquid runs away from the bottom perforated section of the central tube near the bottom potted end 64 and towards the side of the membrane vessel 342. The liquid drains between the potted ends and the membrane vessel 342, passing the membrane modules and entering the gas inlet plenum 355. To allow flow around the potted ends, the mechanical seals 78 can be omitted or can be intermittent or porous seals.

Figure 8:
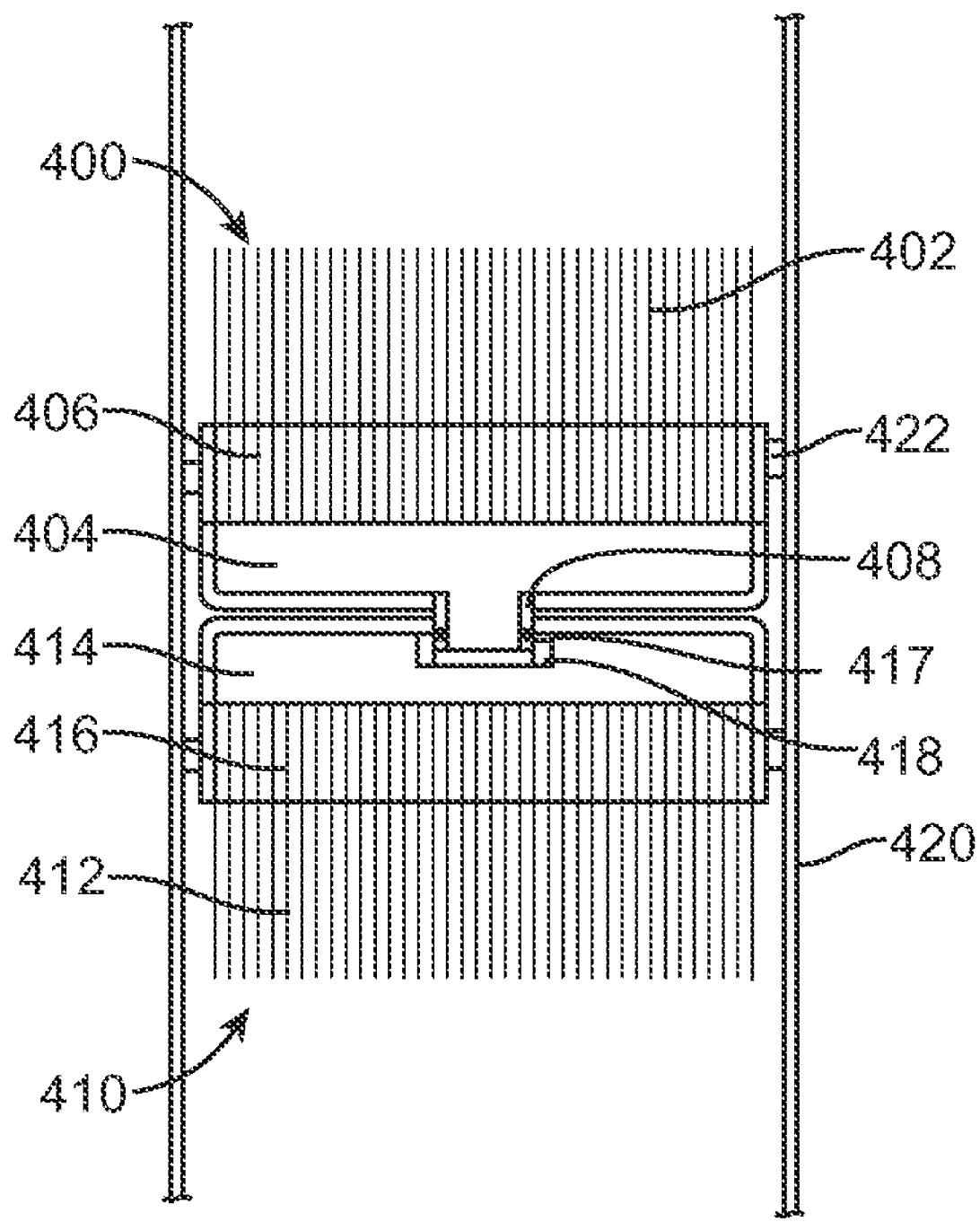
FIG. 8 is a detail cross-section view of a connection arrangement between membrane modules.
Figure 9:
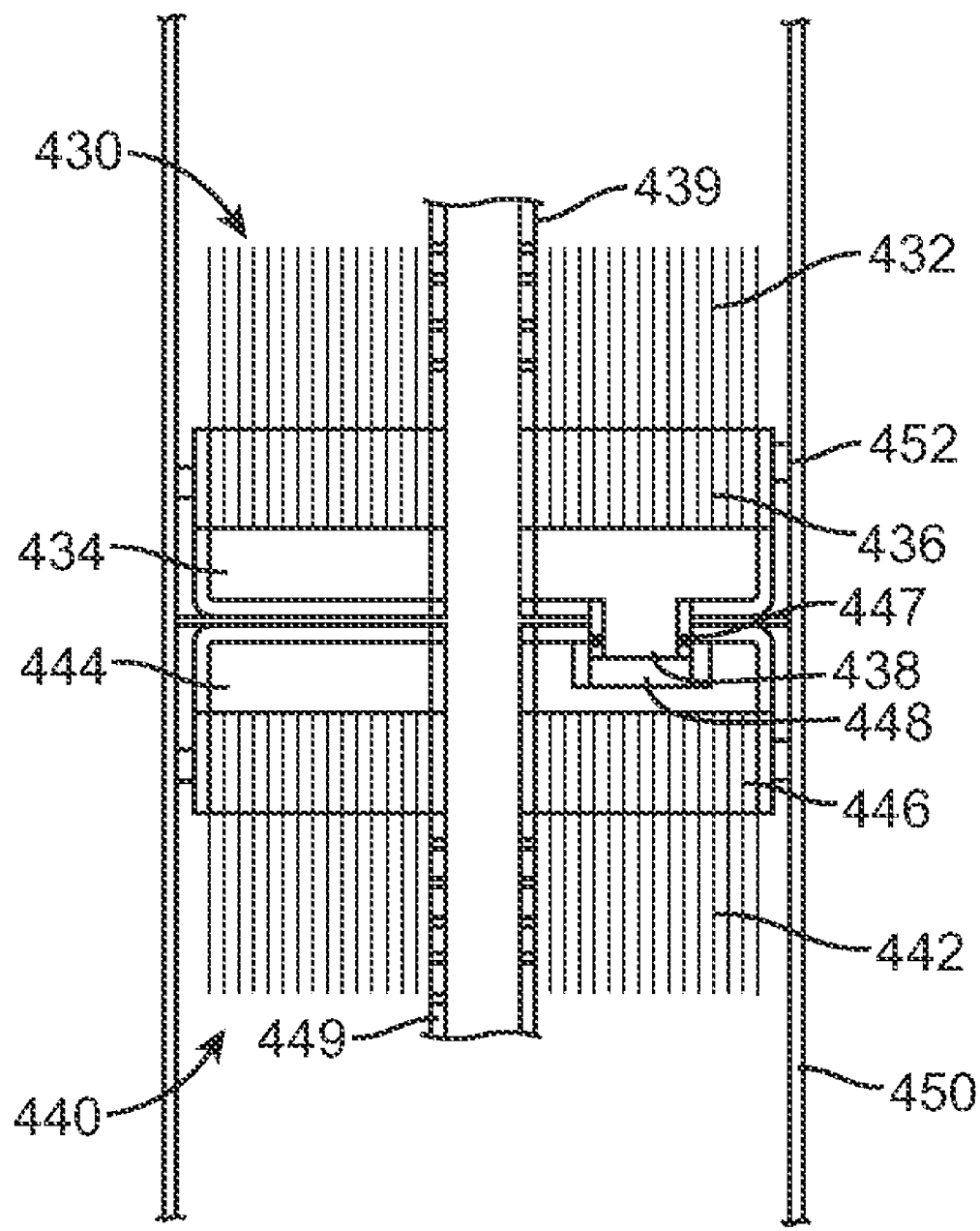
FIG. 9 is a detail cross-section view of another connection arrangement between membrane modules.
Figure 10:
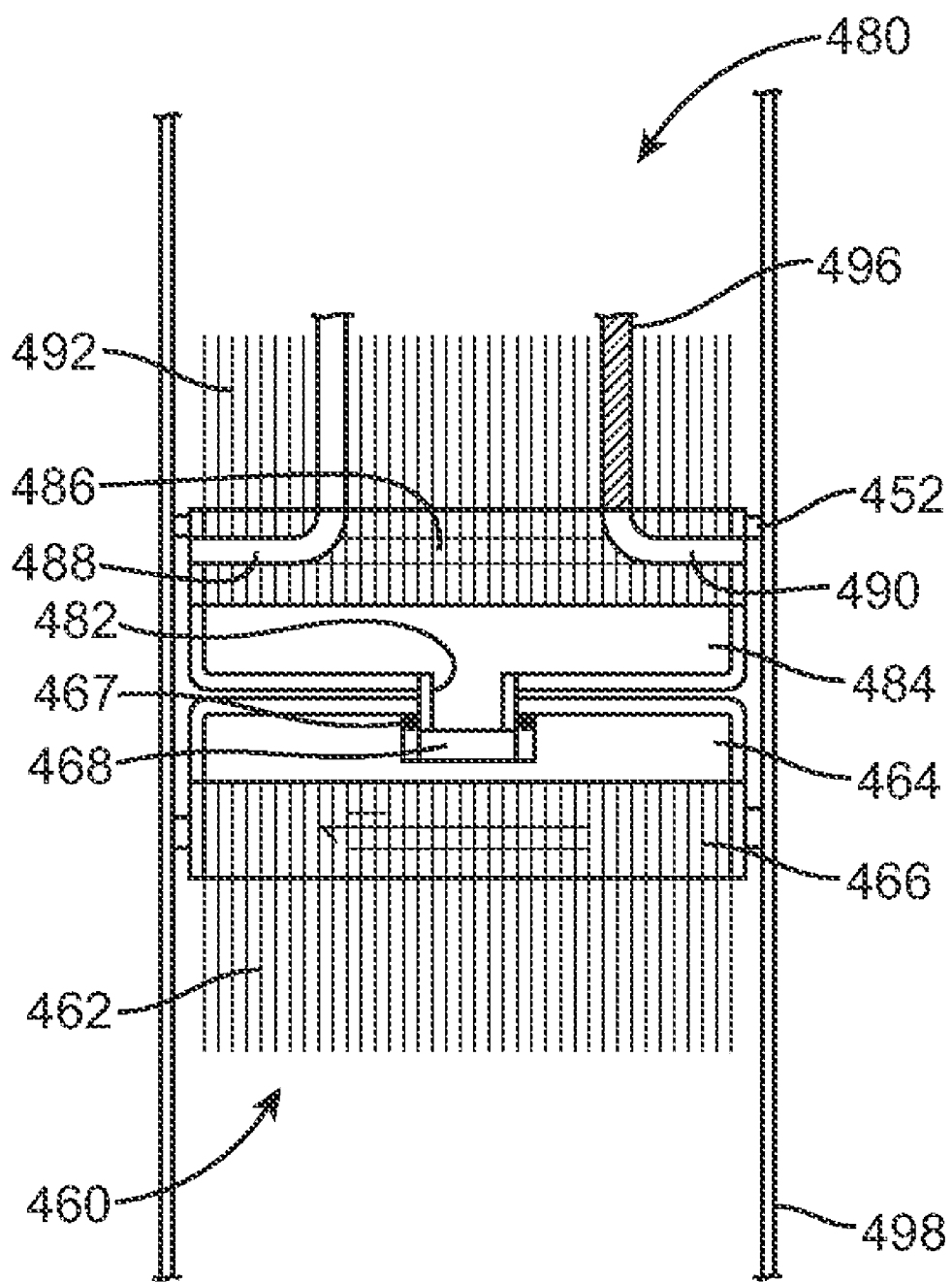
FIG. 10 is a detail cross-section view of another connection arrangement between membrane modules.

FIGS. 8-10 illustrate additional connection arrangements between membrane modules. In these embodiments, adjacent membrane modules are in contact. This saves space since there is no plenum between the adjacent membrane modules.

FIG. 8 is a detail cross-section view of a connection arrangement between membrane modules. In this embodiment, one of the membrane modules has an extension that is mateable with an opening in the adjacent membrane module. The top membrane module 400 has hollow fibers 402 with hollow fiber lumens in communication with a liquid chamber 404 through a potted end 406. An extension 408 in communication with the liquid chamber 404 protrudes from the membrane module 400. The bottom membrane module 410 has hollow fibers 412 with hollow fiber lumens in communication with a liquid chamber 414 through a potted end 416. An opening 418 in communication with the liquid chamber 414 extends into the membrane module 410.

When the membrane modules are assembled into an axial stack within the membrane vessel 420, adjacent membrane modules are in contact with each other and the extension 408 is disposed in the opening 418. Those skilled in the art will appreciate that suitable seals, such as an O-ring 417 about the extension 408 or the like, can be provided between the membrane module 400 and the membrane module 410 to separate the process liquid from the process gas. Spacers 422 can be used to stabilize the membrane modules within the membrane vessel 420. The spacers 422 can be intermittent to allow flow between the membrane vessel 420 and the potted ends. In one embodiment, process liquid flows through the hollow fiber lumens and process gas flows about the outside of the hollow fibers.

FIG. 9 is a detail cross-section view of another connection arrangement between membrane modules. In this embodiment, one of the membrane modules has an extension that is mateable with an opening in the adjacent membrane module, and the outsides of the hollow fibers in adjacent membrane modules are in communication through a central tube. The top membrane module 430 has hollow fibers 432 with hollow fiber lumens in communication with a liquid chamber 434 through a potted end 436. An extension 438 in communication with the liquid chamber 434 protrudes from the membrane module 430. A central tube 439 with perforations above the potted end 436 passes through the liquid chamber 434 and the potted end 436. The bottom membrane module 440 has hollow fibers 442 with hollow fiber lumens in communication with a liquid chamber 444 through a potted end 446. An opening 448 in communication with the liquid chamber 444 extends into the membrane module 440. A central tube 449 with perforations below the potted end 446 passes through the liquid chamber 444 and the potted end 446.

When the membrane modules are assembled into an axial stack within the membrane vessel 450, adjacent membrane modules are in contact with each other, the extension 438 is disposed in the opening 448, and the central tube 439 is aligned with the central tube 449. Those skilled in the art will appreciate that suitable seals, such as an O-ring 447 about the extension 438 or the like, can be provided between the membrane module 430 and the membrane module 440 to separate the process liquid from the process gas. Spacers 452 can be used to stabilize the membrane modules within the membrane vessel 450. The spacers 452 can be intermittent to allow flow between the membrane vessel 450 and the potted ends. In one embodiment, process liquid flows through the hollow fiber lumens and process gas flows through the central tubes and about the outside of the hollow fibers.

FIG. 10 is a detail cross-section view of another connection arrangement between membrane modules. In this embodiment, one of the membrane modules has an extension that is mateable with an opening in the adjacent membrane module, and side tubes through the potted end of one of the membrane modules permits gas flow from the area between the potted end and the membrane vessel to the outsides of the hollow fibers. The bottom membrane module 460 has hollow fibers 462 with hollow fiber lumens in communication with a liquid chamber 464 through a potted end 466. An opening 468 in communication with the liquid chamber 464 extends into the membrane module 460.

The top membrane module 480 includes an extension 482, a liquid chamber 484, a potted end 486 defining side tubes 488, 490, hollow fibers 492, and support rods 496. Support rods 496 connect the one potted end 486 of the membrane module 480 to the opposite potted end of the membrane module 480. The extension 482 in communication with the liquid chamber 484 protrudes from the membrane module 480. The side tubes 488, 490 communicate from the area between the potted end 486 and the membrane vessel 498 to the inter-fiber space outside of the hollow fibers 492.

When the membrane modules are assembled into an axial stack within the membrane vessel 498, adjacent membrane modules are in contact with each other, and the extension 482 is disposed in the opening 468. Those skilled in the art will appreciate that suitable seals, such as an O-ring 467 about the extension 482 or the like, can be provided between the membrane module 460 and the membrane module 480 to separate the process liquid from the process gas. Spacers 452 can be used to stabilize the membrane modules within the membrane vessel 498 and to create a pressure drop to drive the process gas into the side tubes 488, 490. The spacers 452 can be intermittent or porous to allow flow between the membrane vessel 450 and the potted ends.

Process gas flows from the hollow fibers 462 of the membrane module 460, past the area between the potted end 466 and the membrane vessel 498, past the area between the potted end 486 and the membrane vessel 498, through the side tubes 488, 490, and between the hollow fibers 492. In one example, the side tube 488 opens into the inter-fiber space between the hollow fibers 492 at the potted end 486. In another example, the support rod 496 is hollow and perforated, and the side tube 490 opens into the hollow of the support rod 496. The process gas flows from the side tube 490, through the support rod 496, and into the intra-fiber space between the hollow fibers 492 along the support rod 496. Those skilled in the art will appreciate that the perforations in the support rod 496 can be arranged as desired for a particular application, such as at one end, both ends, or along the whole support rod. In another embodiment, the support rod 496 can comprise a gas permeable membrane.

Figure 11:
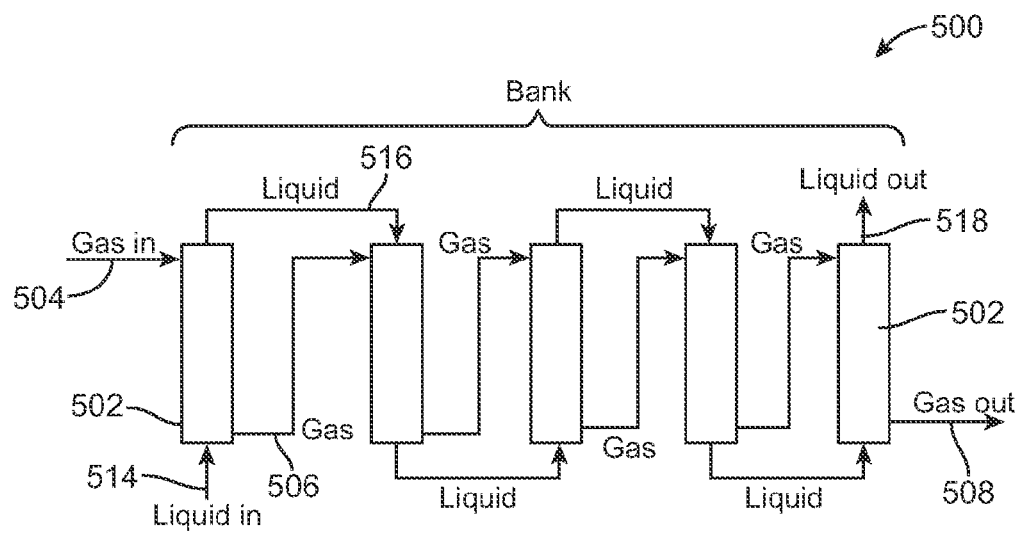
FIG. 11 is a schematic diagram of bioreactor systems connected in series using stacked membrane modules within vertical containment vessels.
Figure 12:
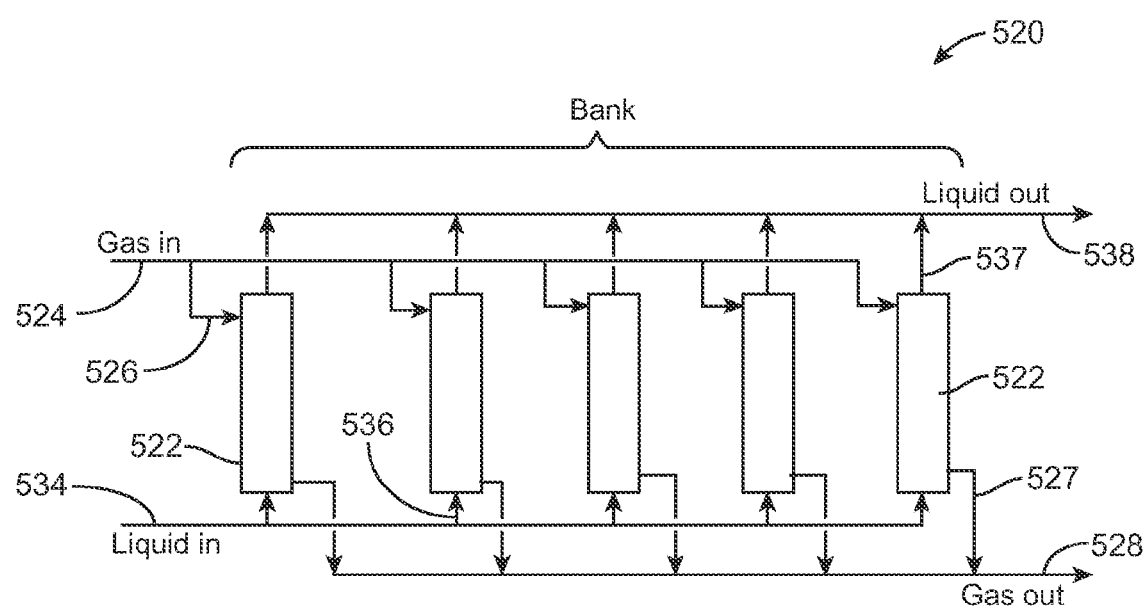
FIG. 12 is a schematic diagram of bioreactor systems connected in parallel using stacked membrane modules within vertical containment vessels.

FIGS. 11 & 12 illustrate combining bioreactor systems into banks. FIG. 11 is a schematic diagram of bioreactor systems connected in series using stacked membrane modules. FIG. 12 is a schematic diagram of bioreactor systems connected in parallel using stacked membrane modules.

Referring to FIG. 11, a number of modular bioreactors 502, each including at least two axially stacked membrane modules, are connected serially to form a bank 500 of multiple membrane vessels. In this embodiment, the process gas enters the bank gas inlet 504, passes through the first bioreactor 502, and passes through the intermediate gas line 506 to the adjacent bioreactor. This is repeated until the process gas exits the last bioreactor 502 through the bank gas outlet 508. The process liquid enters the bank liquid inlet 514, passes through the first bioreactor 502, and passes through the intermediate liquid line 516 to the adjacent bioreactor. This is repeated until the process liquid exits the last bioreactor 502 through the bank liquid outlet 518. The bank liquid outlet 518 can be connected to a product recovery system to recover liquid product from the process liquid. Those skilled in the art will appreciate that the intermediate piping and flows can be selected as desired for a particular application.

Referring to FIG. 12, a number of modular bioreactors 522, each including at least two axially stacked membrane modules, are connected in parallel into a bank 520 of multiple membrane vessels. In this embodiment, the process gas enters bank gas inlet 524, passes through gas inlet branch lines 526, the bioreactors 522, gas outlet branch lines 527, and out bank gas outlet 528. The process liquid enters bank liquid inlet 534, passes through liquid inlet branch lines 536, the bioreactors 522, liquid outlet branch lines 537, and out bank liquid outlet 538. The bank liquid outlet 538 can be connected to a product recovery system to recover liquid product from the process liquid. Those skilled in the art will appreciate that the intermediate piping and flows can be selected as desired for a particular application.

A bioreaction method includes retaining a process gas in a membrane vessel under anaerobic conditions; maintaining multiple membrane modules in the process gas as a stacked arrangement, the membrane modules having a plurality of hollow fibers, each of the plurality of hollow fibers having a hollow fiber wall defining a hollow fiber lumen and an outer surface; growing a biolayer containing microorganisms about the outer surface of the hollow fibers by using at least a portion of the process gas as feed to the microorganisms; and passing a process liquid into the hollow fiber lumens and circulating process liquid from the hollow fiber lumens across the hollow fiber walls to interact with the biolayer and generate a liquid product that mixes with the process liquid. The biolayer can include microorganisms selected from the group consisting of *Clostridium ragsdalei, Butyribacterium methylotrophicum, Clostridium ljungdahlii, Clostridium carboxidivorans*, and combinations thereof. In one embodiment, the membrane modules are two-headed membrane modules having a first potted end and a second potted end, the process liquid flows through the hollow fiber lumens of the hollow fibers from the first potted end to the second potted end, and the process gas flows serially through the membrane modules outside the hollow fibers from the second potted end to the first potted end of adjacent membrane modules. The method can further include recovering the liquid product from the process liquid.

While the embodiments of the invention disclosed herein are presently considered to be preferred, various changes and modifications can be made without departing from the scope of the invention. For example, the direction of flow for the process gas and/or the process liquid can be up or down through the membrane modules, and can be concurrent or countercurrent. The scope of the invention is indicated in the appended claims, and all changes that come within the meaning and range of equivalents are intended to be embraced therein.

The invention claimed is:

1. A modular membrane bioreactor for anaerobic conversion of gas into liquid products comprising:
   a plurality of axially stacked membrane modules having a plurality of hollow fibers packed across a transverse cross sectional area of the membrane module in a direction transverse to a longitudinal axis of the membrane module in a fiber bundle, each of the plurality of hollow fibers having a gas permeable hollow fiber wall defining a hollow fiber lumen and an outer surface, the fibers being potted at least one end in a potting material and the space between fibers within the fiber bundle defining an intra-fiber bundle volume;
   a membrane vessel having an interior sealed from ambient atmosphere for retaining the membrane modules stacked in the membrane vessel in the same axial direction as the hollow fibers extend and surrounded by a process gas in communication about the outer surface of the hollow fiber wall for formation of a biolayer by interaction of microorganisms with the process gas and for production of a liquid product, the membrane vessel having a vessel cross sectional area perpendicular to the longitudinal axis of the membrane vessel of no more than 1.5 times the transverse cross sectional area of the membrane module and an inner diameter greater than the exterior diameter of the membrane modules to space the membrane vessel apart from the membrane modules;

a liquid supply conduit for communicating a process liquid with the hollow fiber lumens of the hollow fibers for permeation of water and nutrients to the biolayer and permeation of liquid product from the biolayer into admixture with the process liquid;

a liquid recovery conduit operably connected to the hollow fiber lumens for recovering the process liquid containing the liquid product that permeates from the biolayer across at least a portion of the hollow fiber wall;

a gas supply conduit for supplying the process gas to the interior of the membrane vessel; and, a plurality of side tubes extending through the potting material of at least one potted end of the membrane module and adapted to communicate process gas through the potted end of the membrane module with the area between the potted end and the membrane vessel and the intra-fiber bundle volume.

2. The bioreactor of claim 1 wherein the hollow fibers comprise an asymmetric membrane wall defining a porous layer of biopores about the outer surface of the membrane wall and a less permeable hydration layer around the hollow fiber lumen, and the porous biopores being open to the outer surface of the hollow fibers and containing the biolayer.

3. The bioreactor of claim 1 wherein:
the gas supply conduit is operably connected to the interior of the membrane vessel surrounding the hollow fibers to supply the process gas containing at least one of CO or a mixture of CO2 and H2; and,
the membrane vessel retains the membrane modules in an anaerobic environment for the formation of the biolayer containing microorganisms selected from the group consisting of *Clostridium ragsdalei*, *Butyribacterium methylotrophicum*, *Clostridium ljungdahlii*, *Clostridium carboxidivorans*, and combinations thereof, and for the production of the liquid product selected from the group consisting of ethanol, n-butanol, hexanol, acetic acid, butyric acid, and combinations thereof.

4. The bioreactor of claim 1 further comprising a product recovery system operably connected to receive the process liquid from the membrane vessel, to separate the liquid product from the process liquid, and to return the process liquid to the membrane vessel.

5. The bioreactor of claim 1 wherein: the membrane module is a two-headed membrane module having a first potted end spaced apart from a second potted end, the first potted end is operably connected to one end of the hollow fibers, and the second potted end is operably connected to the other end of the hollow fibers, to allow the process liquid to flow through the hollow fiber lumens from the first potted end to the second potted end.

6. The bioreactor of claim 5 wherein the hollow fiber lumens extend vertically and the process liquid flows in a principally downward direction through the hollow fiber lumens.

7. The bioreactor of claim 5 wherein the hollow fibers have a length equal to 1.015 to 1.15 times the distance between the first potted end and the second potted end to produce slack in the hollow fibers.

8. The bioreactor of claim 5 wherein:
a conduit communicates the process liquid from one membrane module in the vessel to an adjacent membrane module;
the membrane modules further comprise a bottom liquid chamber operably connected to the first potted end and a top liquid chamber operably connected to the second potted end; and
the top liquid chamber of at least one membrane module communicates with the bottom liquid chamber of the adjacent membrane module.

9. The bioreactor of claim 1 wherein the membrane vessel includes at least one purge outlet in communication with the interior of the membrane vessel for draining liquid from the bottom of the membrane vessel and the continuous gas flow path provides a channel for liquid to flow past the first and second potted ends of the membrane modules.

10. The bioreactor of claim 1 wherein:
the plurality of axially stacked membrane modules is a plurality of two-headed membrane modules axially aligned and connected in series, each of the two-headed membrane modules having a first potted end spaced apart from a second potted end, the first potted end being operably connected to one end of the hollow fibers and the second potted end being operably connected to the other end of the hollow fibers to allow the process liquid to flow through the hollow fiber lumens from the first potted end to the second potted end;
the two-headed membrane modules are operably connected so that process liquid flows serially through the hollow fiber lumens of the plurality of two-headed membrane modules; and
the two-headed membrane modules are operably connected over the length of the membrane vessel to contact the outer surface of the hollow fibers in each membrane module with the process gas.

11. The bioreactor of claim 10 wherein each of the plurality of two-headed membrane modules further comprises a bottom liquid chamber operably connected to the first potted end and a top liquid chamber operably connected to the second potted end.

12. The bioreactor of claim 1 wherein the membrane vessel retains the membrane modules in a vertical stack and the membrane vessel includes at least one purge outlet in communication with the interior of the membrane vessel for draining liquid from the membrane vessel.

13. The bioreactor of claim 12 wherein the membrane modules when inserted in the membrane vessel provide at least one continuous flow path for the liquid to drain from the hollow fibers to the purge outlet.

14. A modular membrane bioreactor for anaerobic conversion of gas into liquid products comprising:
a plurality of axially stacked membrane modules having a plurality of hollow fibers packed across a transverse cross sectional area of the membrane module in a direction transverse to a longitudinal axis of the membrane module in a fiber bundle, each of the plurality of hollow fibers having a gas permeable hollow fiber wall defining a hollow fiber lumen and an outer surface, the fibers being potted at both ends in a potting material and the space between fibers within the fiber bundle defining an intra-fiber bundle volume and each membrane module having a first potted end and a second potted with the first potted end operably connected to one end of the hollow fibers and the second potted end operably connected to the other end of the hollow fibers in an arrangement that can communicate liquid flow through the hollow fiber lumens, through the first potted end, and through the second potted end;

a membrane vessel having an interior sealed from ambient atmosphere for retaining the membrane modules stacked in the membrane vessel in the same axial direction as the hollow fibers extend and surrounded by a process gas in communication about the outer surface of the hollow fiber wall for formation of a biolayer by interaction of microorganisms with the process gas and for production of a liquid product, the membrane vessel having a vessel cross sectional area perpendicular to the longitudinal axis of the membrane vessel of no more than 1.5 times the transverse cross sectional area of the membrane module and an inner diameter greater than the exterior diameter of the potted ends of the membrane modules to space the membrane vessel apart from the membrane modules and to establish a space between the membrane vessel and the potted end of the membrane modules adapted for communication of process gas;

a liquid supply conduit for communicating a process liquid with the hollow fiber lumens of the hollow fibers for permeation of water and nutrients to the biolayer and permeation of liquid product from the biolayer into admixture with the process liquid;

a liquid recovery conduit operably connected to the hollow fiber lumens for recovering the process liquid containing the liquid product that permeates from the biolayer across at least a portion of the hollow fiber wall;

a gas supply conduit for supplying the process gas to the interior of the membrane vessel; and, a plurality of side tubes extending through the potting material of at least one potted end of the membrane module and adapted to communicate process gas through the potted end of the membrane module with the space between the potted end and the membrane vessel and the intra-fiber bundle volume.

* * * * *